(12) United States Patent
Sun et al.

(10) Patent No.: US 8,734,421 B2
(45) Date of Patent: *May 27, 2014

(54) METHODS OF TREATING PORES ON THE SKIN WITH ELECTRICITY

(75) Inventors: Ying Sun, Belle Mead, NJ (US); Jeffrey Wu, Warrington, PA (US); Jue-Chen Liu, Belle Mead, NJ (US); Joseph B. Phipps, Sunnyvale, CA (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/875,032

(22) Filed: Jun. 23, 2004

(65) Prior Publication Data

US 2005/0010192 A1    Jan. 13, 2005

Related U.S. Application Data

(63) Continuation-in-part of application No. 10/685,282, filed on Oct. 14, 2003, now Pat. No. 7,476,221, which is a continuation-in-part of application No. 10/609,727, filed on Jun. 30, 2003, now Pat. No. 7,480,530.

(51) Int. Cl.
*A61M 31/00* (2006.01)
(52) U.S. Cl.
USPC ............................................. 604/501
(58) Field of Classification Search
USPC ........... 604/20, 21, 22, 19, 289, 500, 501, 61, 604/890.1–892.1; 424/78.1, 78.2, 648, 649, 424/448–449; 607/115, 120, 149, 152, 98, 607/75, 289, 39, 43, 20; 601/1, 2
See application file for complete search history.

(56) References Cited

U.S. PATENT DOCUMENTS

| | | | |
|---|---|---|---|
| 3,957,452 A | 5/1976 | Schaer et al. |
| 3,981,747 A | 9/1976 | Doniat et al. |
| 4,067,342 A | 1/1978 | Burton |
| 4,123,511 A | 10/1978 | Heintze |
| 4,167,416 A | 9/1979 | Zolla |
| 4,211,222 A | 7/1980 | Tapper |
| 4,223,661 A | 9/1980 | Sergev et al. |
| 4,305,390 A | 12/1981 | Swartz |

(Continued)

FOREIGN PATENT DOCUMENTS

| EP | 0 337 642 A | 10/1989 |
|---|---|---|
| EP | 0532451 A1 | 3/1993 |

(Continued)

OTHER PUBLICATIONS

WO 00/47274, date: 2000.*

(Continued)

*Primary Examiner* — Manuel Mendez

(57) ABSTRACT

The present invention features a method of treating pores on the skin by applying to skin in need of such treatment a device including a housing having a skin contacting surface, a first conductive electrode, a second conductive electrode, and a carrier; wherein the first conductive electrode is in electric communication with the second conductive electrode, wherein the first conductive electrode is in ionic communication with the carrier, wherein the carrier is in communication with the skin contacting surface, and wherein the skin contacting surface is placed in contact with the skin.

9 Claims, 11 Drawing Sheets

(56) References Cited

U.S. PATENT DOCUMENTS

| | | | |
|---|---|---|---|
| 4,372,296 A | 2/1983 | Fahim | |
| 4,406,658 A | 9/1983 | Lattin et al. | |
| 4,431,500 A | 2/1984 | Messing et al. | |
| 4,474,570 A | 10/1984 | Ariura et al. | |
| 4,606,354 A | 8/1986 | Jacob | |
| 4,665,054 A | 5/1987 | Pickart | |
| 4,689,039 A | 8/1987 | Masaki | |
| 4,760,051 A | 7/1988 | Pickart | |
| 4,764,164 A * | 8/1988 | Sasaki | 604/20 |
| 4,767,401 A | 8/1988 | Seiderman | |
| 4,795,631 A | 1/1989 | Sheehan | |
| 4,810,693 A | 3/1989 | Pickart | |
| 4,842,577 A | 6/1989 | Konno et al. | |
| 4,852,571 A | 8/1989 | Gadsby et al. | |
| 4,877,770 A | 10/1989 | Pickart | |
| 4,895,727 A | 1/1990 | Allen | |
| 4,921,583 A | 5/1990 | Sewell et al. | |
| 4,956,184 A | 9/1990 | Kross | |
| 4,957,480 A | 9/1990 | Morenings | |
| 4,970,252 A | 11/1990 | Sakuta et al. | |
| 4,979,938 A * | 12/1990 | Stephen et al. | 604/20 |
| 5,042,975 A | 8/1991 | Chien et al. | |
| 5,084,006 A * | 1/1992 | Lew et al. | 604/20 |
| 5,122,418 A | 6/1992 | Nakane et al. | |
| 5,135,913 A | 8/1992 | Pickart | |
| 5,147,297 A | 9/1992 | Myers et al. | |
| 5,162,043 A | 11/1992 | Lew et al. | |
| 5,224,927 A | 7/1993 | Tapper | |
| 5,231,169 A | 7/1993 | Constantz et al. | |
| 5,298,017 A | 3/1994 | Theeuwes et al. | |
| 5,304,403 A | 4/1994 | Schlesinger et al. | |
| 5,314,502 A | 5/1994 | McNichols et al. | |
| 5,322,520 A | 6/1994 | Milder | |
| 5,326,341 A | 7/1994 | Lew et al. | |
| 5,338,412 A | 8/1994 | Burk et al. | |
| 5,348,943 A | 9/1994 | Pickart | |
| 5,352,315 A | 10/1994 | Carrier et al. | |
| 5,356,632 A | 10/1994 | Gross et al. | |
| 5,380,272 A | 1/1995 | Gross | |
| 5,382,431 A | 1/1995 | Pickart | |
| 5,384,134 A | 1/1995 | Kross et al. | |
| 5,387,189 A | 2/1995 | Gory et al. | |
| 5,389,220 A | 2/1995 | Herzog et al. | |
| 5,405,317 A | 4/1995 | Myers et al. | |
| 5,412,004 A | 5/1995 | Tachibana et al. | |
| 5,415,628 A * | 5/1995 | Untereker et al. | 604/20 |
| 5,416,364 A | 5/1995 | Divjak | |
| 5,428,185 A | 6/1995 | Kunimoto et al. | |
| 5,443,441 A | 8/1995 | De Claviere | |
| 5,466,217 A | 11/1995 | Myers et al. | |
| 5,470,349 A | 11/1995 | Kleditsch et al. | |
| 5,487,884 A | 1/1996 | Bissett et al. | |
| 5,498,248 A | 3/1996 | Milder | |
| 5,503,840 A | 4/1996 | Jacobson et al. | |
| 5,505,949 A | 4/1996 | Benitez | |
| 5,550,183 A | 8/1996 | Pickart | |
| 5,595,750 A | 1/1997 | Jacobson et al. | |
| 5,601,750 A | 2/1997 | Domke et al. | |
| 5,624,415 A * | 4/1997 | Cormier et al. | 604/290 |
| 5,624,425 A | 4/1997 | Gray et al. | |
| 5,637,084 A | 6/1997 | Kontturi et al. | |
| 5,648,389 A | 7/1997 | Gans et al. | |
| 5,653,989 A | 8/1997 | Sattler | |
| 5,654,362 A | 8/1997 | Schulz, Jr. et al. | |
| 5,678,545 A | 10/1997 | Stratbucker | |
| 5,685,837 A | 11/1997 | Horstmann | |
| 5,688,233 A | 11/1997 | Hofmann et al. | |
| 5,759,564 A | 6/1998 | Milder et al. | |
| 5,760,116 A | 6/1998 | Kilgour et al. | |
| 5,811,487 A | 9/1998 | Schulz, Jr. et al. | |
| 5,817,044 A | 10/1998 | Evers et al. | |
| 5,830,175 A * | 11/1998 | Flower | 604/20 |
| 5,843,186 A | 12/1998 | Christ | |
| 5,855,570 A | 1/1999 | Scherson et al. | |
| 5,897,522 A | 4/1999 | Nitzan | |
| 5,928,185 A | 7/1999 | Muller et al. | |
| 5,931,996 A | 8/1999 | Reisser et al. | |
| 5,935,598 A | 8/1999 | Sage et al. | |
| 5,955,017 A | 9/1999 | Foffano et al. | |
| 5,955,067 A * | 9/1999 | Oge et al. | 424/78.07 |
| 5,961,483 A | 10/1999 | Sage et al. | |
| 5,964,936 A | 10/1999 | Reisser | |
| 5,974,344 A | 10/1999 | Shoemaker, II | |
| 5,985,308 A | 11/1999 | Burrell et al. | |
| 5,993,435 A | 11/1999 | Haak et al. | |
| 5,993,526 A | 11/1999 | Sommer et al. | |
| 6,004,309 A | 12/1999 | Phipps | |
| 6,017,553 A | 1/2000 | Burrell et al. | |
| 6,038,485 A | 3/2000 | Axelgaard | |
| 6,060,000 A | 5/2000 | Milder et al. | |
| 6,078,842 A | 6/2000 | Gross et al. | |
| 6,104,950 A | 8/2000 | Higo et al. | |
| 6,113,636 A | 9/2000 | Ogle | |
| 6,120,756 A | 9/2000 | Markowitz | |
| 6,157,858 A | 12/2000 | Gross et al. | |
| 6,169,920 B1 | 1/2001 | Haak et al. | |
| 6,185,453 B1 | 2/2001 | Hussain et al. | |
| 6,218,350 B1 | 4/2001 | Beggs et al. | |
| 6,223,076 B1 | 4/2001 | Tapper | |
| 6,231,830 B1 | 5/2001 | Madray | |
| 6,238,381 B1 | 5/2001 | Tapper | |
| 6,241,561 B1 | 6/2001 | Zebermann et al. | |
| 6,248,449 B1 | 6/2001 | Watanabe | |
| RE37,263 E | 7/2001 | Kross et al. | |
| 6,273,875 B1 | 8/2001 | Siman et al. | |
| 6,275,372 B1 | 8/2001 | Vassallo et al. | |
| 6,287,484 B1 | 9/2001 | Hausslein et al. | |
| 6,289,241 B1 | 9/2001 | Phipps | |
| 6,294,186 B1 | 9/2001 | Beerse et al. | |
| 6,302,874 B1 | 10/2001 | Zhang et al. | |
| 6,306,384 B1 * | 10/2001 | Lahanas et al. | 424/78.1 |
| 6,317,629 B1 | 11/2001 | Haak et al. | |
| 6,322,588 B1 | 11/2001 | Ogle et al. | |
| 6,383,523 B1 | 5/2002 | Murad | |
| 6,385,487 B1 | 5/2002 | Henley | |
| 6,410,062 B1 | 6/2002 | Callaghan et al. | |
| 6,421,561 B1 | 7/2002 | Morris | |
| 6,424,862 B1 | 7/2002 | Brown, III et al. | |
| 6,443,978 B1 | 9/2002 | Zharov | |
| 6,444,212 B1 | 9/2002 | Cavazzuti et al. | |
| 6,455,065 B1 | 9/2002 | Hymes | |
| 6,475,472 B2 | 11/2002 | Joiner et al. | |
| 6,488,965 B1 | 12/2002 | Karageozian | |
| 6,494,900 B1 | 12/2002 | Salansky et al. | |
| 6,495,158 B1 | 12/2002 | Buseman et al. | |
| 6,522,918 B1 | 2/2003 | Crisp et al. | |
| 6,544,401 B1 | 4/2003 | Colic | |
| 6,552,895 B1 | 4/2003 | Vassallo et al. | |
| 6,560,483 B1 | 5/2003 | Kumar et al. | |
| 6,582,416 B2 | 6/2003 | Tapper | |
| 6,584,349 B1 | 6/2003 | Sage, Jr. et al. | |
| 6,605,751 B1 | 8/2003 | Gibbins et al. | |
| 6,629,947 B1 | 10/2003 | Sahatjian et al. | |
| 6,631,294 B2 | 10/2003 | Andino et al. | |
| 6,632,342 B1 | 10/2003 | Teshima et al. | |
| 6,653,014 B2 | 11/2003 | Anderson et al. | |
| 6,654,635 B1 | 11/2003 | Koga et al. | |
| 6,673,374 B2 | 1/2004 | Murad | |
| 6,708,050 B2 | 3/2004 | Carim | |
| 6,734,155 B1 | 5/2004 | Herbots et al. | |
| 6,735,470 B2 * | 5/2004 | Henley et al. | 604/20 |
| 6,738,662 B1 * | 5/2004 | Frank | 604/20 |
| 6,745,071 B1 | 6/2004 | Anderson et al. | |
| 6,766,202 B2 | 7/2004 | Underwood et al. | |
| 6,775,570 B2 | 8/2004 | Joshi | |
| 6,818,212 B2 | 11/2004 | Johansen | |
| 6,821,281 B2 | 11/2004 | Sherman et al. | |
| 6,821,333 B2 | 11/2004 | Zimmermann et al. | |
| 6,855,117 B2 | 2/2005 | Skover | |
| 6,866,856 B2 | 3/2005 | Lu et al. | |
| 6,890,553 B1 | 5/2005 | Sun et al. | |
| 6,989,156 B2 | 1/2006 | Gillis | |
| 7,005,408 B2 | 2/2006 | Ahmad et al. | |
| 7,008,647 B2 | 3/2006 | Burrell et al. | |

(56) References Cited

U.S. PATENT DOCUMENTS

| | | | |
|---|---|---|---|
| 7,018,660 B2 | 3/2006 | Murad | |
| 7,172,812 B2 | 2/2007 | Greiwe et al. | |
| 7,177,693 B2 | 2/2007 | Starkebaum | |
| 7,220,316 B2 | 5/2007 | Kitsuwa | |
| 7,271,199 B1 | 9/2007 | Quinn et al. | |
| 7,332,246 B2 | 2/2008 | Wiepen | |
| 7,387,807 B2 | 6/2008 | Callaghan et al. | |
| 7,457,667 B2 | 11/2008 | Skiba | |
| 7,476,221 B2 | 1/2009 | Sun et al. | |
| 7,476,222 B2 | 1/2009 | Sun et al. | |
| 7,477,938 B2 | 1/2009 | Sun et al. | |
| 7,477,939 B2 | 1/2009 | Sun et al. | |
| 7,477,940 B2 | 1/2009 | Sun et al. | |
| 7,477,941 B2 | 1/2009 | Sun et al. | |
| 7,479,133 B2 | 1/2009 | Sun et al. | |
| 7,480,530 B2 * | 1/2009 | Sun et al. | 604/20 |
| 7,486,989 B2 | 2/2009 | Sun et al. | |
| 7,495,146 B2 | 2/2009 | Crisp | |
| 7,507,228 B2 | 3/2009 | Sun et al. | |
| 7,507,285 B2 | 3/2009 | Venturini et al. | |
| 8,025,673 B1 | 9/2011 | Lyapko | |
| 8,150,525 B2 | 4/2012 | Fassih et al. | |
| 8,239,017 B2 | 8/2012 | Sun et al. | |
| 2001/0012510 A1 | 8/2001 | Fishman | |
| 2002/0082694 A1 | 6/2002 | McKay | |
| 2002/0099320 A1 | 7/2002 | Beck | |
| 2002/0173743 A1 | 11/2002 | Tapper | |
| 2002/0173833 A1 | 11/2002 | Korman et al. | |
| 2002/0182485 A1 | 12/2002 | Anderson et al. | |
| 2002/0183685 A1 | 12/2002 | Crawford et al. | |
| 2002/0188241 A1 | 12/2002 | Morris et al. | |
| 2003/0019501 A1 | 1/2003 | Hirota et al. | |
| 2003/0023270 A1 | 1/2003 | Danz et al. | |
| 2003/0028170 A1 | 2/2003 | Anderson et al. | |
| 2003/0035955 A1 | 2/2003 | Yadav | |
| 2003/0039860 A1 | 2/2003 | Cheon et al. | |
| 2003/0049536 A1 | 3/2003 | Wiepen | |
| 2003/0054046 A1 | 3/2003 | Burrell et al. | |
| 2003/0059673 A1 | 3/2003 | Langan et al. | |
| 2003/0100884 A1 | 5/2003 | Deagle | |
| 2003/0108612 A1 | 6/2003 | Xu et al. | |
| 2003/0149393 A1 | 8/2003 | Joshi | |
| 2003/0176832 A1 | 9/2003 | Rossi | |
| 2003/0216783 A1 | 11/2003 | Lehtoluoto | |
| 2004/0006374 A1 | 1/2004 | Mondin | |
| 2004/0043062 A1 | 3/2004 | Sun | |
| 2004/0044384 A1 | 3/2004 | Leber et al. | |
| 2004/0086474 A1 | 5/2004 | Rabe et al. | |
| 2004/0110738 A1 | 6/2004 | Gillis et al. | |
| 2004/0115239 A1 | 6/2004 | Shastri et al. | |
| 2004/0138712 A1 | 7/2004 | Tamarkin et al. | |
| 2004/0167460 A1 | 8/2004 | Anderson et al. | |
| 2004/0167461 A1 | 8/2004 | Nitzan et al. | |
| 2004/0208902 A1 | 10/2004 | Gupta | |
| 2004/0213820 A1 | 10/2004 | Yokoi et al. | |
| 2004/0219124 A1 | 11/2004 | Gupta | |
| 2004/0223932 A1 | 11/2004 | Hedgpeth et al. | |
| 2004/0265395 A1 | 12/2004 | Sun et al. | |
| 2004/0267169 A1 | 12/2004 | Sun et al. | |
| 2004/0267189 A1 | 12/2004 | Marr et al. | |
| 2004/0267190 A1 | 12/2004 | Tamarkin et al. | |
| 2004/0267231 A1 | 12/2004 | Sun et al. | |
| 2004/0267232 A1 | 12/2004 | Sun et al. | |
| 2004/0267236 A1 | 12/2004 | Sun et al. | |
| 2004/0267237 A1 | 12/2004 | Sun et al. | |
| 2005/0004508 A1 | 1/2005 | Sun et al. | |
| 2005/0004509 A1 | 1/2005 | Sun et al. | |
| 2005/0004550 A1 | 1/2005 | Sun et al. | |
| 2005/0008861 A1 | 1/2005 | Yadav et al. | |
| 2005/0010161 A1 | 1/2005 | Sun et al. | |
| 2005/0010192 A1 | 1/2005 | Sun et al. | |
| 2005/0015042 A1 | 1/2005 | Sun et al. | |
| 2005/0064176 A1 | 3/2005 | Terry | |
| 2005/0112759 A1 | 5/2005 | Radisic et al. | |
| 2005/0123620 A1 | 6/2005 | Chiou | |
| 2005/0126338 A1 | 6/2005 | Yadav | |
| 2005/0148996 A1 | 7/2005 | Sun et al. | |
| 2005/0175649 A1 | 8/2005 | Disalvo et al. | |
| 2005/0186151 A1 | 8/2005 | Giroud | |
| 2005/0187580 A1 | 8/2005 | Skiba | |
| 2006/0015052 A1 | 1/2006 | Crisp | |
| 2006/0015053 A1 | 1/2006 | Crisp | |
| 2006/0024338 A1 | 2/2006 | Hegedus et al. | |
| 2006/0042509 A1 | 3/2006 | Henglein et al. | |
| 2006/0110415 A1 | 5/2006 | Gupta | |
| 2006/0133134 A1 | 6/2006 | Doyle et al. | |
| 2006/0159643 A1 | 7/2006 | Jacquier | |
| 2006/0204581 A1 | 9/2006 | Gower et al. | |
| 2006/0222595 A1 | 10/2006 | Mukherjee et al. | |
| 2006/0229711 A1 | 10/2006 | Yan et al. | |
| 2006/0263308 A1 | 11/2006 | Brown et al. | |
| 2006/0264804 A1 | 11/2006 | Karmon et al. | |
| 2007/0003516 A1 | 1/2007 | Almond et al. | |
| 2007/0060862 A1 | 3/2007 | Sun et al. | |
| 2007/0065392 A1 | 3/2007 | Simonnet | |
| 2007/0077312 A1 | 4/2007 | Berchert et al. | |
| 2007/0092462 A1 | 4/2007 | Russ et al. | |
| 2007/0122461 A1 | 5/2007 | Ko | |
| 2007/0141173 A1 | 6/2007 | Miyamoto et al. | |
| 2007/0172438 A1 | 7/2007 | Kruger et al. | |
| 2007/0182438 A1 | 8/2007 | Khandros et al. | |
| 2007/0185541 A1 | 8/2007 | DiUbaldi et al. | |
| 2007/0191756 A1 | 8/2007 | Tapper | |
| 2007/0203534 A1 | 8/2007 | Tapper | |
| 2007/0207335 A1 | 9/2007 | Karandikar et al. | |
| 2007/0219606 A1 | 9/2007 | Moreci et al. | |
| 2007/0270942 A1 | 11/2007 | Thomas | |
| 2008/0014247 A1 | 1/2008 | Lu et al. | |
| 2008/0038216 A1 | 2/2008 | Zukowski et al. | |
| 2008/0039770 A1 | 2/2008 | Francis et al. | |
| 2008/0050448 A1 | 2/2008 | Wilson et al. | |
| 2008/0050452 A1 | 2/2008 | Chen et al. | |
| 2008/0125838 A1 | 5/2008 | Francis | |
| 2008/0127990 A1 | 6/2008 | Thevenet | |
| 2008/0249638 A1 | 10/2008 | Asgari | |
| 2008/0311165 A1 | 12/2008 | Gabbay | |
| 2008/0312579 A1 | 12/2008 | Chang et al. | |
| 2009/0017082 A1 | 1/2009 | Morimitsu et al. | |
| 2009/0035342 A1 | 2/2009 | Karandikar et al. | |
| 2009/0045720 A1 | 2/2009 | Lee et al. | |
| 2009/0123733 A1 | 5/2009 | Ohrlander et al. | |
| 2009/0149426 A1 | 6/2009 | Lee et al. | |
| 2009/0292328 A1 | 11/2009 | Birkill et al. | |
| 2009/0304811 A1 | 12/2009 | Xia et al. | |
| 2010/0034767 A1 | 2/2010 | Trabelsi | |
| 2010/0082088 A1 | 4/2010 | Fassih et al. | |
| 2010/0092408 A1 | 4/2010 | Breyfogle et al. | |
| 2010/0172724 A1 | 7/2010 | Hort et al. | |
| 2010/0209515 A1 | 8/2010 | Chantalat et al. | |
| 2010/0209525 A1 | 8/2010 | Chantalat et al. | |
| 2010/0249927 A1 | 9/2010 | Yang et al. | |
| 2010/0268335 A1 | 10/2010 | Yang et al. | |
| 2011/0060419 A1 | 3/2011 | Choi et al. | |
| 2011/0118655 A1 | 5/2011 | Fassih et al. | |
| 2011/0195100 A1 | 8/2011 | Bruning et al. | |
| 2011/0212042 A1 | 9/2011 | Maitra et al. | |
| 2011/0236491 A1 | 9/2011 | Chantalat et al. | |
| 2011/0287075 A1 | 11/2011 | Chantalat et al. | |
| 2012/0015048 A1 | 1/2012 | Maitra et al. | |
| 2012/0021014 A1 | 1/2012 | Chantalat et al. | |
| 2012/0089232 A1 | 4/2012 | Choi et al. | |
| 2012/0148633 A1 | 6/2012 | Sun et al. | |

FOREIGN PATENT DOCUMENTS

| | | | |
|---|---|---|---|
| EP | 800382 B1 | 10/1997 | |
| EP | 1008365 A1 | 6/2000 | |
| EP | 1 249 222 A1 | 10/2002 | |
| EP | 1484012 A1 | 12/2004 | |
| EP | 1677843 B1 | 7/2006 | |
| EP | 1513491 B1 | 2/2009 | |
| EP | 1 291 939 B1 | 8/2011 | |
| EP | 2353578 A2 | 8/2011 | |
| EP | 1 990 377 A1 | 2/2012 | |

(56) References Cited

FOREIGN PATENT DOCUMENTS

| | | |
|---|---|---|
| FR | 2 932 983 A1 | 1/2010 |
| GB | 1270410 | 4/1972 |
| GB | 2206493 A | 1/1989 |
| JP | 61-18708 | 1/1986 |
| JP | 03080874 A | 4/1991 |
| JP | 7233017 | 9/1995 |
| JP | 8196461 A | 8/1996 |
| JP | 10024108 A | 1/1998 |
| JP | 11060417 | 3/1999 |
| JP | 2008-69097 A | 3/2008 |
| RU | 45627 | 5/2005 |
| WO | 89/01764 A1 | 3/1989 |
| WO | 91/16034 A1 | 10/1991 |
| WO | 91/16035 A1 | 10/1991 |
| WO | WO93/00959 A1 | 1/1993 |
| WO | 93/14813 A1 | 8/1993 |
| WO | WO94/11058 A1 | 5/1994 |
| WO | 94/16765 A1 | 8/1994 |
| WO | WO94/17853 A1 | 8/1994 |
| WO | 95/23588 A1 | 9/1995 |
| WO | WO98/14237 A1 | 4/1998 |
| WO | 98/29158 A1 | 7/1998 |
| WO | 99/20229 A1 | 4/1999 |
| WO | WO99/56819 A1 | 11/1999 |
| WO | 00/07658 A1 | 2/2000 |
| WO | WO 00/12173 A1 | 3/2000 |
| WO | 00/37071 A1 | 8/2000 |
| WO | 00/47274 A1 | 8/2000 |
| WO | WO97/06847 A1 | 8/2000 |
| WO | WO 00/62856 A1 | 10/2000 |
| WO | WO 00/62857 A1 | 10/2000 |
| WO | 00/74695 | 12/2000 |
| WO | WO 00/74772 A1 | 12/2000 |
| WO | 01/87267 A1 | 11/2001 |
| WO | WO01/80945 A1 | 11/2001 |
| WO | WO 03/082095 A1 | 10/2002 |
| WO | 02/092167 A1 | 11/2002 |
| WO | WO 02/098502 A2 | 12/2002 |
| WO | 03/032959 A1 | 4/2003 |
| WO | 03/066016 A1 | 8/2003 |
| WO | 03/082095 A1 | 10/2003 |
| WO | WO99/43382 A1 | 11/2003 |
| WO | 2005/004979 | 1/2005 |
| WO | 2005/004981 A2 | 1/2005 |
| WO | 2005/004982 A2 | 1/2005 |
| WO | 2005/004983 A2 | 1/2005 |
| WO | WO 2005/004984 A1 | 1/2005 |
| WO | 2005/023206 | 3/2005 |
| WO | 2006/048879 A1 | 5/2006 |
| WO | 2006/056984 A2 | 6/2006 |
| WO | 2006/072834 A2 | 7/2006 |
| WO | 2006/133134 A2 | 12/2006 |
| WO | 2007/003516 A2 | 1/2007 |
| WO | 2007/048772 A1 | 5/2007 |
| WO | 2008/019116 A2 | 2/2008 |
| WO | 2008/079898 A1 | 7/2008 |
| WO | 2009/045720 A2 | 4/2009 |
| WO | 2009/045750 A1 | 4/2009 |
| WO | 2010/027792 A8 | 3/2010 |
| WO | 2010/051918 A2 | 5/2010 |
| WO | 2010/111502 A2 | 9/2010 |
| WO | 2010/111511 A1 | 9/2010 |
| WO | 2011/059915 A1 | 5/2011 |

OTHER PUBLICATIONS

WO 94/16765, date: 1994.*
Data sheet ionto Patch publicly available prior to Jun. 30, 2003.
Electrochemistry Handbook Table 14.1, McGraw Hill Inc. 1995 pp. 14.3-14.16.
G. Stux, B. Berman, B. Pomeranz, Basics of Acupuncture, Springer 2003 pp. 306-309.
R. Davis, Can Acupuncture Punch Up Your Appearance? Wall Street Journal Health article published Dec. 21, 2004. pp. D7.
P. Spacciapoli, D. Buxton, D. Rothstein, P. Friden, Antimicrobial activity of silver nitrate against periodoental pathogens, Journal of Peridontal Research, 2001, 36:108-113.
International Search Report for PCT/US2004/020382 dated Nov. 4, 2004 for publication No. WO2005/004979.
Ultrafine Zinc and Nickel, Palladium, Silver Coated Zinc Particles Used for Reductive Dehalogenation of Chlorinated Ethylenes In Aqueous Solution, Weifeng Li and Kenneth J. Klabunde, Croatica Chemica Acta CCACAA 71 (4) 843-872 (1998).
Zhu Zhenguo Ed., "The Utility of Physical Therapy", *Nanjing Press*, 1st version (Jan. 1997), p. 75, lines 1 and 12-14.
Michels et al., "Copper Alloys for Human Infectious Disease Control", Presented at Materials Science and Technology Conference, Sep. 25-28, 2005, Pittsburgh, PA, Copper for the 21st Century Symposium.
Anonymous: "Zinc dust XL—Premium Data Sheet", US Zinc Products, Oct. 20, 2003. XP002661863. Retrieved from the Internet: URL:http://www.uszinc.com/en-US/zincdust/Documents/Pdf/XLPremiumTypeIII.pdf.
ASM Handbook, vol. 7: Powder Metal Technologies and Applications (by Asm International Handbook Committee, edited by Peter W. Lee, 1998, pp. 31-109, 311-320.
Bajzer, M. et al., Obesity and Gut Flora, Nature, vol. 444, Dec. 21-28, 2006, p. 1009-1010.
Barrow, G.J. "The Electromotive Force of Chemical Cells", Physical Chemistry, Fourth Edition, McGraw-Hill Book Company (1979) p. 626.
Bell et al., Cell Signal.; 15(1):1-7 (2003).
"Brass" by Collins English Dictionary, http://www.xrefplus.com/entry/hcengdict/brass, accessed Sep. 18, 2012.
Chun et al., Carcinogenesis 25:445-454 (2004).
Degarmo, et al., Materials and Processes in Manufacturing, 8th Ed., Prentice-Hall, 1997, p. 1096-1110.
Fenton MJ, Int J Immunopharmacol 14:401-411 (1992).
Ferry et al., The Effects of Common Anti-Inflammatory Drugs on the Healing Rat Patellar Tendon, The American Journal of Sports Medicine, vol. 35, No. 8, pp. 1326-1333 (2007).
Flournoy et al., Methods Find Exp Clin Pharmacol 12:541-544 (1990).
Garay et al., Journal of the American Academy of Dermatology, vol. 60, Issue 3, Supplement 1, p. AB28 (Mar. 2009).
Goette et al., South Med J. 70:620-622 (1977).
Guy, R. H., Arch. Dermatol Res, 273:91-95 (1982).
Hamamoto et al., Exp Dermatol 2:231-235 (1993).
Hamilton, T.K., Skin Augmentation and Correction: The New Generation of Dermal Fillers—A Dermatologist's Experience, Clinics in Dermatology, 2009:27, S13-S22.
Jacobs, et al., Corrosion of Metal Orthopaedic Implants, The J. of Bone and Joint Surgery (American), 1998, p. 80:268-82.
Jumbelic et al., Skin Pharmacol Physiol. 19:147-152 (2006).
Kaczmar, J.W., et al., The production and application of metal matrix composite materials, Journal of Materials Processing Technology, vol. 106, Issues 1-3, 2000, p. 58-67.
Kollias et al., Photochem Photobiol. 56:223-227 (1992).
Kruger, Electrochemistry of Corrosion, Electrochemistry Encyclopedia, Apr. 2001, p. 1-10.
Lavoie et al., Light-Induced Byproducts of Vitamin C in Multivitamin Solutions, Clinical Chemistry, 50:1, 135-140 (2004).
Li Y., Food Chem Toxicol., 34:887-904 (1996).
Ligier et al., Corrosion Science 41:1139-1164 (1999).
Ly Chan et al., "Treatment of Palmar Hyperhidrosis Using Tap Water Iontophoresis: Local Experience": HKMJ, vol. 5, No. 2, Jun. 1999.
Mastrangelo et al., Exposure to Hydrogen Peroxide and Eye and Nose Symptoms Among Workers in a Beverage Processing Plant, Am. Occup. Hyg. Oxford Univ. Press, pp. 1-5 (2008).
Matula et al., J Int Med Res., 16:98-106 (1988).
Miyoshi et al., Age-dependent cell death and the role of ATP in hydrogen peroxide-induced apoptosis and necrosis, PNAS, vol. 103, No. 6, pp. 1727-1731 (Feb. 2006).
Park, H., et al., Effects of electrical stimulation in C2C12 muscle Constructs, J. Tissue Engineering and Regenerative Medicine 2(5)2008, p. 279-287.

(56) References Cited

OTHER PUBLICATIONS

Procellera™ bioelectric wound dressing, Vomaris Wound Care, Inc., distributed Oct. 22-25, 2009 at 2009 Clinical Symposium on Advances in Skin and Wound Care, San Antonio, TX.
Remington's Pharmaceutical Sciences, Chp. 84, "Emulsions", pp. 1507-1511 (1985).
Sato et al., Generation and transit pathway of H+ is critical for inhibition of palmar sweating by iontophoresis in water, J. Applied Physiology, Nov. 1993; 75:2258-2264.
Schreiber et al., Surgery 138:940-946 (2005).
Sheenan et al., Theory and Practice of Histo-technology (St. Louis: CV Mosby, 1980) pp. 223-277.
Stamatas et al., Blood stasis contributions to the perception of skin pigmentation, Journal Biomedical Optics 9(2), pp. 315-322 (Mar./Apr. 2004).
Stux et al., Basics of Acupuncture, Springer 2003 pp. 306-309.
Sun et al., Intestinal Electric Stimulation Decreases Fat Absorption in Rats: Therapeutic Potential for Obesity, Obesity Research, vol. 12, No. 8, Aug. 2004, p. 1235-1242.
Sur et al., J Invest Dermatol. 128(2):336-344 (2008).
T. Johnson, CRC Ethnobotany Desk Reference, 1998 Ed, p. 198-199.
T. Johnson, CRC Ethnobotany Desk Reference, 1998 Ed, p. 516-517.
T. Johnson, CRC Ethnobotany Desk Reference, 1998 Ed, p. 823-824.
Yang et al., Mycopathologia 148:79-82 (1999).
Zhang, Corrosion and Electrochemistry of Zinc, 1996, p. 217-236.
Cosmetic Metallic Powder VISIONAIRE Honey Technical Data Sheet, Mar. 1, 2005, XP55041377.
Cosmetic Metallic Powder VISIONAIRE Natural Gold Technical Data Sheet, Mar. 1, 2005, XP55041380.
Eckart, Internet; "Formulation Guidelines for Formulating Effect Pigments in Water Based Gels", Sep. 1, 2009, pp. 1-5 XP55041406.
Fujishima et al., Titanium dioxide photocatalysis, Jun. 29, 2000, Journal of Photochemistry and Photobiology C: Photochemistry Reviews, vol. 1, pp. 1-21.
Hunter et al., the Role of Particles in Stabilizing Foams and Emulsion, Mar. 2008, Advances in Colloid and Interface Science, vol. 137, pp. 57-81.
IMWSCC Presentation (SEPPIC, Interest of Rheology and Texture Technology in Cosmetic Research, Nov. 2008, IMWSCC Presentation, slides 1-54).
Jager-Lezer, N., et al., "Rheological Analysis of Highly Concentrated w/o Emulsions", Rheol Acta, vol. 37, pp. 129-138 (1998) XP002685540.

\* cited by examiner

METHODS OF TREATING PORES ON THE SKIN WITH ELECTRICITY

CROSS REFERENCE TO RELATED APPLICATIONS

This is a continuation-in-part of co-pending application Ser. No. 10/685,282, filed on Oct. 14, 2003, which a continuation-in-part of copending application Ser. No. 10/609,727, filed on Jun. 30, 2003, which are hereby incorporated by reference in its entirety.

BACKGROUND OF THE INVENTION

Transdermal devices have been widely prescribed for decades in the treatment of is systemic diseases and local conditions. During passive transdermal delivery, an active agent is delivered into a mammal by using a concentration gradient across a barrier membrane (e.g., through passive diffusion through skin). For example, a patch containing the drug in high concentration is affixed to the skin of a patient.

Electricity may be employed to facilitate drug transport across the skin barrier. In electricity-assisted devices, an electric potential (voltage) is applied to the membrane to facilitate drug transport. In transdermal iontophoresis, an ionized drug migrates into the skin driven by an applied electric potential gradient. Anionic drugs are delivered into the skin under the cathode (negatively charged electrode), while cationic drugs are delivered under the anode (positively charged electrode). Iontophoresis enables enhanced as well as better control of permeation rate of the ionic species into the skin.

The most common design of an iontophoresis device includes a power source (e.g., a battery), an electric control mechanism, and two separate conductive electrodes. Each conductive electrode is in contact with a separate electrolyte composition (with or without an active agent). The electrolyte or ionic active composition is generally either an aqueous solution contained in a liquid chamber or a semi-solid. The assembly of the conductive electrode and electrolyte composition is often referred to as "an electrode assembly" or simply "an electrode." The two electrode assemblies are usually affixed to the skin separated by electric insulation between them.

Alternatively, the two electrode assemblies may be constructed into a single iontophoresis device with an electric insulating material built between the two electrode assemblies for electrical isolation to prevent shorting current. An example of such an iontophoresis device is disclosed in U.S. Pat. No. 5,387,189.

In another variation of the common iontophoresis device designs, the electrolyte composition in one of the two electrode assemblies is eliminated, and the conductive electrode is placed directly in contact with the skin to complete the electric circuit. An example of such iontophoresis device is disclosed in U.S. Pat. No. 6,385,487.

During a typical iontophoresis operation (mono-polar operation), one of the two electrodes (i.e., active electrode) drives the active agent into the skin. The other electrode (i.e., disperse electrode) serves to close the electrical circuit through the skin. Sometimes, a second active agent of opposite electric charge can be placed into electrolyte composition in contact with the second electrode, thus, being delivered into the skin under the second electrode. Alternatively, the electric polarity of the first and second electrodes can be reversed periodically to drive ionic species under both electrodes (bi-polar operation). A bi-polar iontophoresis device for transdermal drug delivery is disclosed U.S. Pat. No. 4,406,658.

Using a galvanic couple as the power source in iontophoresis device is well known in the art. See e.g., U.S. Pat. Nos. 5,147,297, 5,162,043, 5,298,017, 5,326,341, 5,405,317, 5,685,837, 6,584,349, 6,421,561 and 6,653,014. Typical materials from which a galvanic couple is made includes a zinc donor electrode and a silver chloride counter electrode. Such a combination produces an electric potential of about one volt. Such a galvanic couple powered iontophoresis system, absent some controlling means, activates automatically when body tissue and/or fluids form a complete circuit with the system to generate the electricity.

SUMMARY OF THE INVENTION

In one aspect, the present invention features a method of exfoliating the skin by applying to skin in need of such exfoliating a device including a housing having a skin contacting surface, a first conductive electrode, a second conductive electrode, and a carrier including an agent selected from an alpha-hydroxy acid, beta-hydroxy acid, and salts thereof; wherein the first conductive electrode is in electric communication with the second conductive electrode, wherein the first conductive electrode is in ionic communication with the carrier, wherein the carrier is in communication with the skin contacting surface, and wherein the skin contacting surface is placed in contact with the skin.

In another aspect, the present invention features a method of exfoliating the skin by topically applying a composition including a first conductive electrode in the form of a particulate, a second conductive electrode in the form of a particulate, and an agent selected from an alpha-hydroxy acid, beta-hydroxy acid, and salts thereof wherein the difference of the standard potentials of the first conductive electrode and the second conductive electrode is at least 0.2 V.

In another aspect, the present invention features a method of promoting a composition including a first conductive electrode in the form of a particulate and a second conductive electrode in the form of a particulate wherein the difference of the standard potentials of the first conductive electrode and the second conductive electrode is at least 0.2 V, such method including promoting the topical application of such composition for the treatment of a wound on barrier membrane.

In another aspect, the present invention features a method of treating pores on the skin by applying to skin in need of such treatment a device including a housing having a skin contacting surface, a first conductive electrode, a second conductive electrode, and a carrier; wherein the first conductive electrode is in electric communication with the second conductive electrode, wherein the first conductive electrode is in ionic communication with the carrier, wherein the carrier is in communication with the skin contacting surface, wherein the skin contacting surface is placed in contact with the skin, and wherein and wherein said method of treating pores on the skin is selected from the group of cleansing pores on the skin, reducing sebum on the skin, reducing the appearance of blackheads on the skin, and reducing the appearance of pores on the skin.

In another aspect, the present invention features a method of treating pores on the skin by topically applying a composition including a first conductive electrode in the form of a particulate and a second conductive electrode in the form of a particulate, wherein the difference of the standard potentials of the first conductive electrode and the second conductive electrode is at least 0.2 V.

In another aspect, the present invention features a method of promoting a composition including a first conductive electrode in the form of a particulate and a second conductive electrode in the form of a particulate wherein the difference of the standard potentials of the first conductive electrode and the second conductive electrode is at least 0.2 V, such method including promoting the topical application of such composition for the treatment of pores on the skin, wherein the method of treating pores on the skin is selected from the group of cleansing pores on the skin, reducing sebum on the skin, reducing the appearance of blackheads on the skin, and reducing the appearance of pores on the skin.

In one aspect, the present invention features a method of treating infections of the skin, including but not limited to, acne or rosacea, by applying to the skin electrochemically generated zinc ions. In one embodiment, the method includes topically applying a device including an anode containing zinc. In a further embodiment, the device includes a housing having a skin contacting surface; a first conductive electrode containing zinc; a second conductive electrode; and a carrier; wherein the first conductive electrode is in electric communication with the second conductive electrode, wherein the first conductive electrode is in ionic communication with the carrier, and wherein the carrier is in communication with said skin contacting surface.

In another aspect, the present invention features a device having a barrier membrane contacting surface, the device containing: a power source; a first conductive electrode; a second conductive electrode; and a carrier; wherein the power source is in electric communication with the first conductive electrode and the second conductive electrode, wherein the first conductive electrode and the second conductive electrode are in ionic communication with the carrier, and wherein the carrier is in communication with the barrier membrane contacting surface. In another aspect, the present invention features a method of administering electricity to a human barrier membrane by applying to the membrane such a device. In another aspect, the present invention features a method of treating a skin condition by applying to the skin such a device.

In another aspect, the present invention features a device having a barrier membrane contacting surface, the device containing: a power source; a first conductive electrode; a second conductive electrode; and a carrier containing an active agent; wherein the power source is in electric communication with the first conductive electrode and the second conductive electrode, wherein the first conductive electrode and the second conductive electrode are in ionic communication with the carrier, and wherein the carrier is in communication with the barrier membrane contacting surface. In another aspect, the present invention features a method of administering electricity to a human barrier membrane by applying to the membrane such a device. In another aspect, the present invention features a method of treating a skin condition by applying to the skin such a device.

In another aspect, the present invention features a device having a barrier membrane contacting surface, the device containing: a power source; a first conductive electrode; a second conductive electrode; a first light emitting diode; and a carrier containing an active agent; wherein the power source is in electric communication with the first conductive electrode, the second conductive electrode, and the light emitting diode, and wherein the device is arranged such that light from the first light emitting diode and the carrier are in communication with the barrier membrane contacting surface. In another aspect, the present invention features a method of administering an active agent to a human barrier membrane by applying to the membrane such a device. In another aspect, the present invention features a method of treating a skin condition by applying to the skin such a device.

In another aspect, the present invention features a method of treating a skin condition by applying to the skin a device having a barrier membrane contacting surface that administers an oxidizing agent to the barrier membrane, wherein the device contains: a power source; a first conductive electrode, wherein the first conductive electrode is an inert anode; a second conductive electrode, wherein the second conductive electrode is a cathode; and a carrier containing water; wherein the power source is in electric communication with the first conductive electrode and the second conductive electrode, wherein the first conductive electrode is in ionic communication with the carrier, wherein the oxidizing agent is generated by electric current passing from the first conductive electrode through the carrier, and wherein the carrier is in communication with the barrier membrane contacting surface. In another aspect, the present invention features a method of administering an oxidizing agent to a barrier membrane by applying to the membrane such a device.

In another aspect, the present invention features a method of treating a skin condition by applying to the skin a device having a barrier membrane contacting surface that administers a reducing agent to the barrier membrane, wherein the device contains: a power source; a first conductive electrode, wherein the first conductive electrode is an inert cathode; a second conductive electrode, wherein the second conductive electrode is a anode; and a carrier containing water; wherein the power source is in electric communication with the first conductive electrode and the second conductive electrode, wherein the first conductive electrode is in ionic communication with the carrier, wherein the reducing agent is generated by electric current passing from the first conductive electrode through the carrier, and wherein the carrier is in communication with the barrier membrane contacting surface. In another aspect, the present invention features a method of administering an reducing agent to a barrier membrane by applying to the membrane such a device.

Other features and advantages of the present invention will be apparent from the detailed description of the invention and from the claims.

DETAILED DESCRIPTION OF THE INVENTION

Figure 1:
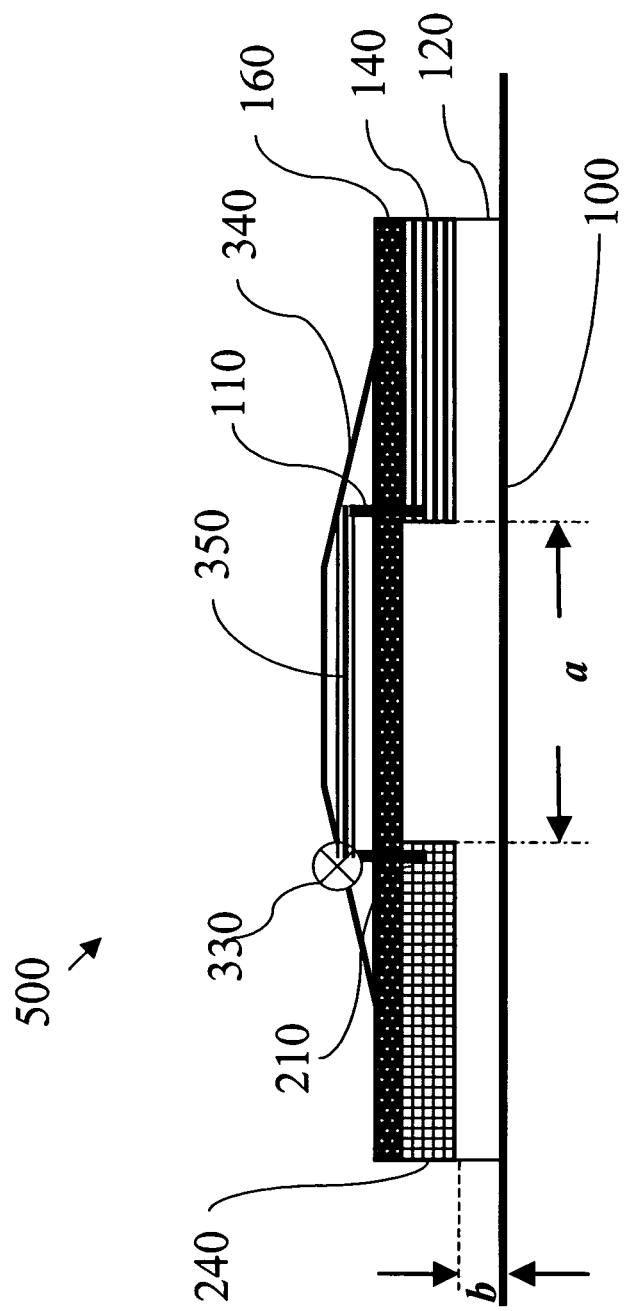
FIG. 1 is a cross-sectional view of one embodiment of the device suitable for practicing the invention. The conductive electrodes 140 and 240 are connected respectively by the lead wires 110 and 210 to electrically insulated connecting wire 350 located at the back of the device 500.

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage refers to a percentage by weight (i.e., % (W/W)).

What is meant by a "product" is a product containing the device in finished packaged form. In one embodiment, the product contains instructions directing the user to apply the device to the barrier membrane (e.g., to treat a skin condition). Such instructions may be printed on the device, label insert, or on any additional packaging.

In one aspect, the present invention features promoting a device of the present invention for its intended use. What is meant by "promoting" is promoting, advertising, or marketing. Examples of promoting include, but are not limited to, written, visual, or verbal statements made on the product or in stores, magazines, newspaper, radio, television, internet, and the like.

As used herein, "pharmaceutically-acceptable" means that the ingredients which the term describes are suitable for use in contact with the barrier membrane (e.g., the skin or mucosa) without undue toxicity, incompatibility, instability, irritation, allergic response, and the like.

As used herein, "safe and effective amount" means an amount of the ingredient or of the composition sufficient to provide the desired benefit at a desired level, but low enough to avoid serious side effects. The safe and effective amount of the ingredient or composition will vary with the area being treated, the age and skin type of the end user, the duration and nature of the treatment, the specific ingredient or composition employed, the particular pharmaceutically-acceptable carrier utilized, and like factors.

As used herein, the term "treating" or "treatment" means the treatment (e.g., alleviation or elimination of symptoms and/or cure) and/or prevention or inhibition of the condition (e.g., a skin condition). What is meant by a "skin condition" is a dermatological disease or disorder (including, but not limited, acne, rosacea, or skin infections) or skin characteristic (including, but not limited to, pigmentation, hair growth regulation, skin texture, skin firmness, skin elasticity, skin vasculature, dark circles, cellulite, sebum regulation, and skin shine). Examples of skin infections include, but are not limited to, those due to susceptible pathogens such as acne, rosacea, impetigo, folliculitis, furunculosis, ecthyma, eczema, psoriasis, atopic dermatitis, herpes, epidermolysis bullosa, icthyosis, and infected traumatic lesions (e.g., ulcers, minor burns, cuts, abrasions, lacerations, wounds, biopsy sites, surgical incisions and insect bites).

The present invention relates to a device for the delivery of electricity (e.g., to induce a desirable biological response) and/or an active agent into a barrier membrane. In one embodiment, the device of the present invention is a self-contained device containing a battery as power source and two conductive electrodes in electric communication with the positive and negative poles of the battery. In one embodiment, the device of the present invention is a self-contained device containing at least a pair of two dissimilar conductive electrodes in electric communication as a power source. By "electric communication" is meant that electrons can directly pass between the elements of the device (e.g., between the conductive electrodes of the device). In one embodiment, the two conductive electrodes are in electric communication via direct contact with each other.

By "ionic communication" it meant that electrons can pass between the elements (e.g., the conductive electrode, the carrier and/or the conductive electrode and the skin) through the migration of ions as "electron movers" in contact with such elements (e.g., electrons pass between the conductive electrode and the skin via ionic transport of electrolytes (e.g., in the carrier) in contact with the conductive electrode and the skin).

In one embodiment, the two conductive electrodes are in ionic communication with the carrier containing an electrolyte (e.g., ions of one or more electrolytes in the carrier are in contact with the conductive electrode) and the carrier is in ionic communication with the skin. This electrode configuration differs from those in conventional iontophoresis devices in which each conductive electrode is in contact with a separate carrier (e.g., each electrode is contained in a separate compartment and affixed to the skin with electric insulation between them in order that all the electric current travels through the skin to complete the electric circuit). An advantage of such an embodiment of the present invention includes the capability of delivering simultaneously active agents of opposite charges from the same carrier into substantially the same skin site under the conductive electrodes. Another advantage is that the devices of the present invention are much easier to manufacture than conventional iontophoresis devices, and therefore, are enable substantial cost-savings.

The device contains a barrier membrane contacting surface (e.g., a skin contacting surface) that is applied to the membrane (e.g., applied by the user to the user's skin). The device is arranged such that carrier is in communication with the barrier membrane contacting surface (e.g., such that electricity and/or the active agent may be administered from the carrier into the barrier membrane). In one embodiment, the carrier is the barrier membrane contacting surface (e.g., the carrier is a hydrogel). In one embodiment, the device contains a light emitting diode such that light from the light emitting diode is in communication with the barrier membrane contacting surface (e.g., such that the light may be administered to the barrier membrane).

In one embodiment, the device of the present invention delivers an active agent into the barrier membrane. The active agents to be delivered by the device of the present invention include active agents either initially incorporated in the carrier or electrochemically generated by the electric current passing from a conductive electrode through the carrier during use. What is meant by "electrochemically generated" is that the chemical specie is created as a result of an electrochemical reaction resulting from electric current flowing through an electrode, such a chemical specie released from a reactive electrode (e.g., an electrochemically generated zinc ion), a chemical specie electrochemically generated on the surface of an inert electrode, or a chemical specie that is a subsequent reaction product of such electrochemically generated specie.

Power Source

In one embodiment, the device of the present invention includes a power source. The power source may be conventional direct current (DC) or pulsed DC, such as that disclosed in U.S. Pat. No. 5,042,975. In one embodiment, the current density to be used by the device in the present invention (current intensity per unit area of the barrier membrane) is generally less than about 0.5 mA/cm$^2$, such as less than about 0.1 mA/cm$^2$ or less than about 0.05 mA/cm$^2$. In one embodiment, the power source produces a voltage of from about 0.1 volts to about 9 volts, such as from about 1 to about 3 volts, such as about 1.5 volts.

In one embodiment, the power source is a battery (e.g., a rechargeable or disposable battery). In one embodiment, the battery is a disposable battery of small size suitable for a wearable patch or facial mask type adhesive device. Examples of suitable batteries include, but not limited to, button or coin batteries such as silver oxide, lithium, and zinc air batteries (which are typically used in small electronic devices). A zinc air battery is preferred because of its small size and high energy density, as well as its environmental friendliness. Examples of zinc air batteries include, but are not limited to, Energizer™ AC5 and AC10/230 (Eveready Battery Co. Inc., St. Louis, Mo.). Another preferred battery for the device is a flexible thin layer open liquid state electrochemical cell battery, such as a battery described in U.S. Pat. No. 5,897,522.

Galvanic Couple

In one embodiment, the device/composition of the present invention has a galvanic couple as its power source, wherein the electrons that pass between the first conductive electrode and the second conductive electrode are generated as a result of the difference of the standard potentials between the electrodes (e.g., the electricity is not generated by an external battery or other power source such as an AC power source). Examples of such galvanic couples include, but are not limited to, zinc-copper, zinc-copper/copper halide, zinc-copper/copper oxide, magnesium-copper, magnesium-copper/copper halide, zinc-silver, zinc-silver/silver oxide, zinc-silver/silver halide, zinc-silver/silver chloride, zinc-silver/silver bromide, zinc-silver/silver iodide, zinc-silver/silver fluoride, zinc-gold, magnesium-gold, aluminum-gold, magnesium-silver, magnesium-silver/silver oxide, magnesium-silver/silver halide, magnesium-silver/silver chloride, magnesium-silver/silver bromide, magnesium-silver/silver iodide, magnesium-silver/silver fluoride, magnesium-gold, aluminum-copper, aluminum-silver, aluminum-silver/silver oxide, aluminum-silver/silver halide, aluminum-silver/silver chloride, aluminum-silver/silver bromide, aluminum-silver/silver iodide, aluminum-silver/silver fluoride, copper-silver/silver halide, copper-silver/silver chloride, copper-silver/silver bromide, copper-silver/silver iodide, copper-silver/silver fluoride, iron-copper, iron-copper/copper oxide, iron-copper/copper halide, iron-silver, iron-silver/silver oxide, iron-silver/silver halide, iron-silver/silver chloride, iron-silver/silver bromide, iron-silver/silver iodide, iron-silver/silver fluoride, iron-gold, iron-conductive carbon, zinc-conductive carbon, copper-conductive carbon, magnesium-conductive carbon, and aluminum-carbon. The materials which serve to make up the galvanic couple may also serve as the conductive electrodes of the device, e.g., zinc as the conductive anode and silver/silver chloride as the conductive cathode or zinc as the conductive anode and copper as the conductive cathode. The metals serve as the galvanic couple and conductive electrodes may also be alloys. Non-limiting examples of the alloys include alloys of zinc, copper, aluminum, magnesium as anode materials, and alloys of silver, copper, gold as cathode materials.

In one embodiment, the materials that make up the galvanic couple have a standard potential difference equal to or greater than about 0.1 volts, such as greater than about 0.2 volts such as greater than about 0.5 volts. In one embodiment, the materials that make up the galvanic couple have a standard potential difference equal to or less than about 3 volts.

In one embodiment, the device or composition of the present invention generates and/or is capable of generating current into the barrier membrane of from about 1 nano-A/cm$^2$ to about 400 micro-A/cm$^2$ of electricity such as from about 100 A/cm$^2$ to about 50 micro A/cm$^2$.

In one embodiment, one of the conductive electrodes is in the form of a metal sheet, a metal wire, or a metal coated on a substrate, and the other conductive electrode is attached or deposited to the first conductive electrode. In a further embodiment, the metal sheet is perforated. In one embodiment, such perforated metal sheet is in the form of a mesh such as a mesh of zinc, magnesium, aluminum, copper, or their alloys thereof. In one embodiment, the second conductive electrode is in the form a fabric coated with a metal, and its oxide, halide, and sulfide, such as a fabric coated with silver, silver/silver oxide, silver/silver halide, zinc, magnesium, copper, copper/copper halide, copper/copper oxide. In another embodiment, the second conductive electrode is deposited to the first conductive electrode by chemical or electrochemical deposition such as electroless plating for chemical deposition and electroplating for electrochemical deposition as known in the art. In a further embodiment, the second conductive electrode is deposited to the first conductive electrode by physical deposition, such as spray coating, plasma coating, conductive ink coating, screen printing, dip coating, or vacuum deposition.

In one embodiment, the device is a single compartment treatment device. What is meant by a "single compartment treatment device" is a device in which both conductive electrodes of the device are in contact with the same carrier. Examples of such devices are shown in FIGS. 1–4 and 6–11.

Carrier

The carrier of the present invention is a liquid (e.g., a solution, a suspension, or an emulsion which may be immobilized within an absorbent material such as gauze or nonwoven pad), a semi-solid (e.g., a gel, a cream, a lotion, microemulsion, or hydrogel), or a solid (e.g., a lyophilized composition containing active agents, which may be reconstituted by adding a liquid prior to use) that during use is capable of conducting electricity from a conducting electrode (e.g., the carrier contains one or more electrolytes, organic solvents, and water). In one embodiment, the carrier (e.g., a liquid or semi-solid) is added to the device by the user prior to applying the device to the barrier membrane.

Examples of electrolytes include, but are not limited to, pharmaceutically acceptable organic and organic salts and buffers. Examples of salts include, but are not limited to, chloride salts (such as sodium chloride, potassium chloride, lithium chloride, calcium chloride, strontium chloride, magnesium chloride or other chloride salts), as well as salts of sodium, potassium, lithium, calcium, magnesium, strontium, fluoride, iodide, bromide. Examples of buffers include, but are not limited to, phosphates, citrates, acetates, lactates, and borates.

In one embodiment, the electrolyte is an active agent, or becomes an active agent after the passage of the electric current through the carrier. Examples of such electrolyte-active agents include, but are not limited to, salicylic acid, salicylates, and other weak acid or weak base active agents.

In one embodiment, the carrier contains water. In a further embodiment, the carrier may also contain one or more organic solvents. Examples of organic solvents include, but are not limited to: dimethyl isosorbide; isopropylmyristate; surfactants of cationic, anionic and nonionic nature; vegetable oils; mineral oils; waxes; gums; synthetic and natural gelling agents; alkanols; glycols; and polyols.

Examples of glycols include, but are not limited to, glycerin, propylene glycol, butylene glycol, pentalene glycol, hexylene glycol, polyethylene glycol, polypropylene glycol, diethylene glycol, triethylene glycol, glycerol, and hexanetriol, and copolymers or mixtures thereof. Examples of alkanols include, but are not limited to, those having from about 2 carbon atoms to about 12 carbon atoms (e.g., from about 2 carbon atoms to about 4 carbon atoms), such as isopropanol and ethanol. Examples of polyols include, but are not limited to, those having from about 2 carbon atoms to about 15 carbon atoms (e.g., from about 2 carbon atoms to about 10 carbon atoms) such as propylene glycol.

The organic solvents may be present in the carrier in an amount, based upon the total weight of the carrier, of from about 1 percent to about 90 percent (e.g., from about 5 percent to about 50 percent). Water may be present in the carrier (prior to use) in an amount, based upon the total weight of the carrier, of from about 5 percent to about 95 percent (e.g., from about 50 percent to about 90 percent).

The carrier may also contain: preservatives (such as cresol, chlorocresol, benzyl alcohol, methyl p-hydroxylbenzoate, propyl p-hydroxybenzoate, phenol, thimerosal, benzalkonium chloride, benzethonium chloride, and phenylmercuric nitrate); stabilizing agents or antioxidants (such as ascorbic acid, ascorbic acid esters, butylhydroxy anisole, butylhydroxy toluene, cysteine, N-acetylcysteine, sodium bisulfite, sodium metabisulfite, sodium formaldehydesulfoxylate, acetone sodium bisulfite, tocopherols, and nordihydroguaiaretic acid); chelating agents (such as ethylenediaminetetraacetic acid and its salts); buffers (such as acetic acid, citric acid, phosphoric acid, glutamic acid, and salts thereof); and tonicity adjusting agents (such as sodium chloride, sodium sulfate, dextrose and glycerin).

In one embodiment, the carrier may also contain a suspending material and/or a fluid-absorbing material (e.g., for physically stabilizing the ingredients of the carrier). Examples of suspending materials include, but are not limited to: cotton-based gauze; non-woven pads made of rayon or a mixture of rayon, polyester and/or other polymer fibers; open-cell foam and sponge-like materials contained of polyurethane, polyester and/or other polymers; and cross-linked and noncross-linked gelling materials, such as polyacrylamide, polyvinyl alcohol, gelatin, hydroxymethylcellulose, hydroxyethylcellulose, hydroxypropylcellulose, methylcellulose, and carboxymethylcellulose.

Examples of fluid-absorbing materials include, but are not limited to: cross-linked and non-cross-linked polymers; swellable polymers such as water-swollen cellulose derivatives (e.g., methylcellulose (MC), hydroxyethyl methylcellulose (HEMA), hydroxypropyl methylkcellulose (HPMC), ethylhydroxyethyl cellulose (EHEC), hydroxyethylcellulose (HEC), hydroxypropylcellulose (HPC), and carboxymethlcellulose (CMC) and their salts); polyvinyl alcohol (PVA); polyvinylpyrrolidone (PVP); polyethylene oxide (PEO); polymers prepared by monomers such as hydroxyethyl methacrylate (HEMA), hydroxyethoxyethyl emthacrylate (HEEMA), hydroxydiethoxyethl methacrylate (HDEEMA), methyoxyethyl methacrylate (MEMA), methoxyethoxyethyl methacrylate (MEEMA), methyldiethoxyethyl methacrylate (MDEEMA), ethylene glycol dimethacrylate (EGDMA), n-vinyl-2pyrrolidone (NVP), methacrylic acid (MA), and vinyl acetate (VAC); polycrylamide; gelatin; gums and polysaccharides such as gum arabic, gum karaya, gum tragacanth, guar gum, gum benzoin, and alginic acid and their salts; polyethylene glycol (PEG); polypropylene glycol (PPG); and clays or other swellable minerals such as bentonite and montmorillonite. The amount of fluid absorbable material in the carrier may range from about 0.1% to about 95%, by weight, such as from about 1% to about 20%, by weight, of the carrier.

Another embodiment of the present invention is directed to pairing one or more inert conductive electrodes in order to electrochemically generate oxidizing or reducing agents from electrochemically reactive materials in situ in the carrier. Such oxidizing or reducing agents can be used as active agents to treat barrier membrane conditions.

Examples of the electrochemically reactive materials in the carrier according to the present invention include, but are not limited to, water and compounds containing the elements selected from the Periodic Table of the Elements VIB and VIIB (such as oxygen, sulfur, fluorine, chlorine, bromine, and iodine).

In one embodiment, the reactive material reacts with the inert anode to form an oxidizing agent. Examples of such a reactive material includes, but is not limited to, the ions $OH^-$, $Cl^-$, $I^-$, $Br^-$, $SO_3^{2-}$, and $HCO_3^-$. The present device, thus, enables to generation of oxidizing agents, such as nascent oxygen (e.g., singlet oxygen), chlorine and chlorine dioxide gases, which are difficult to formulate in a conventional topical product.

In one embodiment, the reactive material reacts with the inert cathode to form a reducing agent. Examples of such a reactive material includes, but is not limited to, oxidized or disulfide forms of thio-compounds with one or more sulfhydryl functional groups, thio-containing amino acids and their salts or esters, and sulfides. Examples of such thio-compounds include, but are not limited to: thioglycolic acid and its salts, such as thioglycolates of calcium, sodium, strontium, potassium, ammonium, lithium, magnesium, and other metal salts; thioethylene glycol; thioglycerol; thioethanol; thioactic acid; and thiosalicylic acid; and their salts. Examples of the thio-containing amino acids include, but are not limited to, L-cysteine, D-cysteine, DL-cysteine, N-acetyl-L-cysteine, DL-homocysteine, L-cysteine methyl ester, L-cysteine ethyl ester, N-carbamoyl cysteine, glutathione, and cysteamine. Examples of sulfides, include but are not limited to, calcium, sodium, potassium, lithium and strontium sulfides and glutathione disulfide. The inert cathode converts the aforementioned reactive oxidized or disulfide form of a sulfur-containing compound to a thio-containing compound, or a sulfydryl-containing compound. Examples of such a conversion is the conversion of cystine to cysteine and the conversion of the oxidized form of glutathione to glutathione.

In one embodiment, the concentration of the reactive material in the carrier may range from about 0.01% to about 25%, by weight, such as from about 0.1% to about 10%, by weight, of the carrier. The pH value of the carrier may range from about pH 1.5 to about pH 9, preferably from pH 2 to pH 7, and most preferably from about pH 3 to pH 5.

In one embodiment, the carrier contains an adhesive. The adhesive is used to affix the device to the barrier membrane. Examples of hydrophobic adhesives include, but are not limited to, silicones, polyisobutylenes and derivatives thereof, acrylics, natural rubbers, and combinations thereof. Examples of silicone adhesives include, but are not limited to, Dow Corning 355 available from Dow Corning of Midland, Mich.; Dow Corningo X7-2920; Dow Corning X7-2960; and GE 6574 available from General Electric Company of Waterford, N.Y. Examples of acrylic adhesives include, but are not limited to, vinyl (D acetate-acrylate) multipolymers such as Gelva 7371, available from Monsanto Company of St. Louis, Mo.; Gelvao 7881; Gelva 2943; and 1-780 medical grade adhesive available from Avery Dennison of Painesville, Ohio. Examples of hydrophilic adhesives include, but are not limited to, gum papaya and other natural gums, MC, HEMA, HPMC, EHEC, HEC, HPC, CMC, PVA, PVP, PEO, HEMA, HEEMA, HDEEMA, MEMA, MEEMA, MDEEMA, EGDMA, NVP MA, VAC, polycrylamide, getatins, gum arabic, gum karaya, gum tragacanth, guar gum, gum benzoin, and alginic acid and their salts, polyethylene glycol (PEG), and polypropylene glycol (PPG).

In one embodiment, the concentration of the adhesive in the carrier may range from about 0.1% to about 95%, by weight, such as from about 1% to about 20%, by weight, of the carrier.

Electrodes

The conductive electrodes of the present invention may be a reactive conductive electrodes or inert conductive electrodes. What is meant by a "reactive conductive electrode" is that the conductive electrode itself goes through a change in its chemical composition during the electrode chemical reactions occurring with the electric current passing through the electrode during the process. In one embodiment, the reactive conductive electrode is an anode made of reactive materials such as a pure metal or a metal alloy including, but not limited to, zinc, aluminum, copper, magnesium, manganese, silver, titanium, tin, iron, and alloys thereof. The materials which serve to make up the galvanic couple described earlier may also serve as the reactive conductive electrode. Upon passage of an electric current, metal ions such as zinc, copper, magnesium, manganese and/or aluminum cations are released from the anode into the carrier and delivered into the barrier membrane. Such ions may serve therapeutic benefits such as anti-microbial effects, immunologic modulation, enzymatic regulation, and/or anti-inflammatory effects.

In one embodiment, the reactive conductive electrode is made of reactive materials such as metal halides (e.g., silver-silver chloride (Ag/AgCl), silver-silver bromide, and silver-silver iodide). In this case, the primary electrochemical reaction at the cathode surface is conversion of solid silver halide to metallic silver with little unwanted consumption of the oxidizing agents generated by the anode. The released halide ions may be subsequently oxidized to oxidizing agents, such as chloride ions to chlorine ($Cl_2$), hypochlorous acid (HClO), and hypochlorite ions ($ClO^-$), and iodide ions to iodine.

What is meant by an "inert conductive electrode" is that the conductive electrode itself does not go through a change in its chemical composition. In one embodiment, the anode is made of an inert conductive electrode, so that the electrochemical process at the surface of the anode generates oxidizing agents such as nascent oxygen (e.g., by electrolysis of water) and/or chlorine-containing oxidizing agents such as chlorine, hypochlorite, chlorate and perchlorate, and chlorine dioxide. Nascent oxygen is an oxidizing agent that is inhibitive to *P. acnes*, and chlorine-containing oxidizing agents are potent antimicrobial agent with bacteriacidal activity.

In one embodiment, the conductive electrode is made of, or coated on the surface with, an inert materials such as noble metals (e.g., gold, platinum, or gold-coated conductive metals), conductive carbon (e.g., glassy carbon or graphite), carbon-embedded polymers (e.g., carbon silicone rubbers), conductive carbon polymer foam or sponge, silver halide-coated silver (e.g., silver chloride-coated silver, silver bromide-coated silver, and silver iodide-coated silver), and corrosive resistant alloys.

In one embodiment, the anode of the device, serving as the conductive electrode, is made of aforementioned reactive conductive oxidizable metals such as zinc, calcium, magnesium, aluminum, iron, tin, copper, or alloys thereof, while the cathode, also serving as the conductive electrode, is made of the aforementioned reactive reducible conductive materials such as a more chemically stable metal and its metal halides, oxide, sulfide or other metal salts, such as silver and silver halides (e.g., silver chloride, silver bromide, silver iodide, silver fluoride), silver oxide, silver sulfide. In one embodiment, the reducible conductive material is in direct contact with a good electric conductor, such as: a thin layer of silver chloride, silver oxide, or silver sulfide over metallic silver; silver chloride powder with a binder (e.g., silver chloride ink); and/or silver chloride powder mixed with silver or conductive carbon powder held together by a binder in a matrix form (e.g., silver-silver chloride ink and silver chloride-carbon ink).

In another embodiment, the anode of the device in the present invention is made of aforementioned reactive conductive oxidizable metals while the cathode is made of aforementioned more chemically stable electrode materials such as conductive carbon, metallic silver, gold or platinum, or a powder mixture of conductive carbon and the noble metal in a matrix form as disclosed in U.S. Pat. No. 5,162,043.

In one embodiment, the device of the present invention enables the targeted delivery of beneficial zinc through hair follicles to the pilosebaceous unit (i.e., a sebaceous gland and the associated hair follicle) to treat acne or rosacea. Zinc is an essential metal to the human body because it participates in various biological activities in the body (e.g., the body of a 70-Kg person contains about 2.3 grams of zinc). It is known that the lack of zinc in the body may lead to skin diseases such as acne.

In another embodiment, the device of the present invention enables the targeted delivery of other beneficial metals into the hair follicles and the pilosebaceous glands by using an anode made of zinc alloy containing small quantities of other beneficial metals. Such beneficial metals includes, without limitation, certain metals essential to the human body such asiron, copper, magnesium, manganese, calcium, potassium, aluminum, and selenium. As the zinc alloy anode oxidizes, it releases into the carrier zinc ions and other beneficial metals in the zinc alloy, which ingredients subsequently migrate into the hair follicles under the applied electric potential over the skin. In one embodiment, the content of the zinc alloy in the anode is greater than about 50% by weight, such as greater than 90% by weight.

In one embodiment, the ratio of the conductance measured between the first conductive and second conductive electrode of (i) the carrier and (ii) the skin hydrated with such carrier (wherein substantially all of the current passes between the electrodes through the skin) is in a range from about 10000:1 to about 1:100. In other words, the electric current distribution between $I_{carrier}$ and $I_{skin}$ is such that the value of $I_{carrier}/I_{skin}$ is between about 10,000 and about 0.01. $I_{carrier}$ is the portion of the total current going through the device ($I_{total}$) that only passes through the carrier layer between the anode and cathode without traveling through the skin, whereas $I_{skin}$ is the portion of $I_{total}$ that passes through the skin, namely, $I_{total}=I_{carrier}+I_{skin}$.

Decreasing the ratio of the conductance of the carrier to the conductance of the skin will result in a greater percentage of current passage through the skin, thereby enhancing iontophoretic delivery of any active agents being so delivered into the skin. Decreasing the conductivity of the carrier can non-exclusively be accomplished by adding less conductive materials to the carrier. Examples of such less conductive materials include, but are not limited to, oils such as silicone or hydrocarbon oils, air pockets such as air bubbles or air pockets in a semi-solid carrier, or polymer or clay beads. In one embodiment where the primary intention is to electrochemically generate species in the carrier, the value of $I_{carrier}/I_{skin}$ is between about 10,000 and about 1. In another embodiment where the primary intention is to deliver electricity and/or active agents into the skin, the value of $I_{carrier}/I_{skin}$ is between about 10 and about 0.01. Adjustment of the value of $I_{carrier}/I_{skin}$ for a particular application can also be achieved by changing the distance between the first and the second electrode, or the distance between the two conductive electrode and the skin. For example, as the distance between the two conductive electrode decreases, the conductance measured between the two electrode increases and so is the $I_{carrier}$, leading to a increased value of $I_{carrier}/I_{skin}$. On the other hand, if the distance between the two conductive electrodes and the skin increases, the $I_{skin}$ increases, leading to decreased value of $I_{carrier}/I_{skin}$.

Electrochemically Generated Zinc Ions

In one embodiment, zinc ions are electrochemically generated by a zinc anode in, or are subsequently added to, a topical composition. The topical composition is then applied to the barrier membrane of the user for the intended beneficial effects from the zinc ions and other active agents present in the topical composition. The active agents in the topical composition may contain anti-acne agents such as salicylic acid or benzoyl peroxide. One method of producing such electrochemically generated zinc ions is to incorporate an electrochemical device for zinc generation into a packaging and/or dispensing container of the topical composition (e.g., bottle equipped with a dispensing pump for an acne-treating/-preventing skin cream). In one embodiment, an electrochemical device including a zinc anode, a silver/silver chloride cathode, and a power source (e.g., a battery) electrically communicating with each other, is included within the dispensing pump. As the topical composition (such as a cream) passes out of the dispensing pump, it comes into contact with both the zinc anode and cathode and completes the electric circuit (i.e., an electric current runs from the anode into the cream, and returns to the power source via the cathode), the zinc anode begins to release zinc ions into the cream. Alternatively, the electrochemical device for zinc generation does not contain a battery. Instead, the zinc anode and cathode are connected to form a galvanic couple to generate zinc ions when both electrodes come into contact with the cream.

Active Agents

In one embodiment, the carrier contains one or more active agents. What is meant by an "active agent" is a compound (e.g., a synthetic compound or a compound isolated from a natural source) that has a cosmetic or therapeutic effect on the barrier membrane and the surrounding tissues (e.g., a material capable of exerting a biological effect on a human body) such as therapeutic drugs, including, but not limited to, organic and macromolecular compounds. Examples of such therapeutic drugs include peptides, polypeptides, proteins, and nucleic acid materials comprising DNA; and nutrients. Examples of polypeptide and protein active agents include thyrotropin-releasing hormone (TRH), vasopressin, gonadotropin-releasing hormone (GnRH or LHRH), melanotropin-stimulating hormone (MSH), calcitonin, growth hormone releasing factor (GRF), insulin, erythropoietin (EPO), interferon alpha, interferon beta, oxytocin, captopril, bradykinin, atriopeptin, cholecystokinin, endorphins, nerve growth factor, melanocyte inhibitor-I, gastrin antagonist, somatotatin, encephalins, melatonin, vaccines, botox (Botulinum neurotoxins), cyclosporin and its derivatives (e.g., biologically active fragments or analogs). Other active agents include anesthetics; analgesics (e.g., fentanyl and salts thereof such fentanyl citrate); drugs for treating psychiatric disorders, epilepsies, and migraine; drugs for stopping drug additions and abuses; anti-inflammatory agents; drugs to treat hypertension, cardiovascular diseases, gastric acidity and ulcers; drugs for hormone replacement therapies and contraceptives such as estrogens and androgens; antibiotics, antifungals, antiviral and other antimicrobial agents; antineoplastic agents, immunosuppressive agents and immunostimulants; and drugs acting on blood and the blood forming argans including hematopoietic agents and anticoagulants, thrombolytics, and antiplatelet drugs. Other active agents that can be delivered into the body using the shear device in the present invention include vaccines for various diseases, such as those for influenza, AIDS, hepatitis, measles, mumps, rubella, rabies, rubella, avercella, tetanus, hypogammaglobulinemia, Rh disease, diphtheria, botulism, snakebite, back widow bite and other insect bite/sting, idiopathic thrombocytopenic purpura (ITP), chronic lymphocytic leukemia, cytomegalovirus (CMV) infection, acute renal rejection, oral polio, tuberculosis, pertussis, Haemophilus b, *Pneumococcus*, and *Staphylococcus aureus*.

In one embodiment, the carrier contains an anti-acne and/or anti-rosacea agent. Examples of anti-acne and anti-rosacea agents include, but are not limited to: retinoids such as tretinoin, isotretinoin, motretinide, adapalene, tazarotene, azelaic acid, and retinol; salicylic acid; benzoyl peroxide; resorcinol; sulfur; sulfacetamide; urea; antibiotics such as tetracycline, clindamycin, metronidazole, and erythromycin; anti-inflammatory agents such as corticosteroids (e.g., hydrocortisone), ibuprofen, naproxen, and hetprofen; and imidazoles such as ketoconazole and elubiol; and salts and prodrugs thereof. Other examples of anti-acne active agents include essential oils, alpha-bisabolol, dipotassium glycyrrhizinate, camphor, β-glucan, allantion, feverfew, flavonoids such as soy isoflavones, saw palmetto, chelating agents such as EDTA, lipase inhibitors such as silver and copper ions, hydrolyzed vegetable proteins, inorganic ions of chloride, iodide, fluoride, and their nonionic derivatives chlorine, iodine, fluorine, and other valences, synthetic phospholipids and natural phospholipids such as Arlasilk™ phospholipids CDM, SV, EFA, PLN, and GLA (Uniqema, ICI Group of Companies, Wilton, UK).

In one embodiment, the device of the present invention contains an anti-aging agent. Examples of suitable anti-aging agents include, but are not limited to: inorganic sunscreens such as titanium dioxide and zinc oxide; organic sunscreens such as octyl-methoxy cinnamates; retinoids; dimethylaminoathanol (DMAE), copper containing peptides, vitamins such as vitamin E, vitamin A, vitamin C, and vitamin B and vitamin salts or derivatives such as ascorbic acid di-glucoside and vitamin E acetate or palmitate; alpha hydroxy acids and their precursors such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrrolactic acid, alpha-hydroxyisovaleric acid, ethyl pyruvate, galacturonic acid, glucoheptonic acid, glucoheptono 1,4-lactone, gluconic acid, gluconolactone, glucuronic acid, glucuronolactone, isopropyl pyruvate, methylpyruvate, mucic acid, pyruvic acid, saccharic acid, saccaric acid 1,4-lactone, tartaric acid, and tartronic acid; beta hydroxy acids such as beta-hydroxybutyric acid, beta-phenyl-lactic acid, and beta-phenylpyruvic acid; zinc and zinc containing compounds such as zinc oxides; and botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, nice, and safflower; and salts and prodrugs thereof.

In one embodiment, the carrier contains a depigmentation agent. Examples of suitable depigmentation agents include, but are not limited to: soy extract; soy isoflavones; retinoids such as retinol; kojic acid; kojic dipalmitate; hydroquinone; arbutin; transexamic acid; vitamins such as niacin and vitamin C; azelaic acid; linolenic acid and linoleic acid; placertia; licorice; and extracts such as chamomile and green tea; and salts and prodrugs thereof.

In one embodiment, the carrier contains a plant extract. Examples of plant extracts include, but are not limited to, feverfew, soy, *glycine soja*, oatmeal, what, aloe vera, cranberry, hazel witch, alnus, arnica, artemisia capillaris, asiasarum root, birch, calendula, chamomile, cnidium, comfrey, fennel, galla rhois, hawthorn, houttuynia, hypericum, jujube, kiwi, licorice, magnolia, olive, peppermint, philodendron, salvia, sasa albo-marginata, natural isoflavonoids, soy isoflavones, and natural essential oils.

In one embodiment, the carrier contains metals such as metal ions, metal salts, metal complexes, fine metal powders, fine metal coated fibers and fabrics of synthetic or natural origin, or fine metal fibers. Examples of such metals include, but are not limited to, zinc, copper, aluminum, gold, silver, titanium. The metal ions provide benefits such as antimicrobial, anti-inflammatory, and/or sebum-reduction effects. The beneficial metal ions may be released from the metal anode as the result of an electrochemical oxidation reaction concurrent with electric current passage (e.g., zinc ions electrochemically generated from a zinc anode).

In another embodiment, the beneficial ions may be generated indirectly from the electrochemical reactions at the electrode surface, such as the generation of hydrogen or hydroxyl ions at an inert electrode, which subsequently leads to a process to generate beneficial ions. For example, a device of the present invention may contain a power source, an inert anode (e.g., platinum, platinum coated conductive electrode, gold, or gold-coated conductive electrode), a reactive cathode (e.g., silver/silver chloride electrode), and an aqueous carrier composition containing an oxide (e.g., zinc oxide particles) among other active agents. During application to the skin, the electrolysis of water at the inert anode produces excess hydrogen ions which acidify the carrier toward a lower pH value, while the electrochemical reaction at the reactive cathode (e.g., the conversion of silver chloride to silver ions) does not affect the pH. As the solution becomes more acidic, the oxide starts to dissolve to release ions (e.g., zinc ions) for their beneficial effects to the barrier membrane.

Other active agents include those commonly used as for topical treatment and in cosmetic treatment of skin tissues, such as topical antibiotics for wounds, topical antifungal drugs to treat fungal infections of the skin and nails, and antipsoriatic drugs to treat psoriatic lesions of the skin and psoriatic nails.

Examples of antifungal drugs include but are not limited to miconazole, econazole, ketoconazole, sertaconazole, itraconazole, fluconazole, voriconazole, clioquinol, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, and their pharmaceutically acceptable salts and prodrugs. In one embodiment, the antifungal drugs are an azole, an allylamine, or a mixture thereof.

Examples of antibiotics (or antiseptics) include but are not limited to mupirocin, neomycin sulfate bacitracin, polymyxin B, 1-ofloxacin, tetracyclines (chlortetracycline hydrochloride, oxytetracycline-10 hydrochloride and tetrachcycline hydrochoride), clindamycin phsphate, gentamicin sulfate, metronidazole, hexylresorcinol, methylbenzethonium chloride, phenol, quaternary ammonium compounds, tea tree oil, and their pharmaceutically acceptable salts and prodrugs.

Examples of antimicrobials include but are not limited to salts of chlorhexidine, such as Iodopropynyl butylcarbamate, diazolidinyl urea, chlorhexidene digluconate, chlorhexidene acetate, chlorhexidene isethionate, and chlorhexidene hydrochloride. Other cationic antimicrobials may also be used, such as benzalkonium chloride, benzethonium chloride, triclocarbon, polyhexamethylene biguanide, cetylpyridium chloride, methyl and benzothonium chloride. Other antimicrobials include, but are not limited to: halogenated phenolic compounds, such as 2,4,4',-trichloro-2-hydroxy diphenyl ether (Triclosan); parachlorometa xylenol (PCMX); and short chain alcohols, such as ethanol, propanol, and the like. In one embodiment, the alcohol is preferably at a low concentration (e.g., less than about 10% by weight of the carrier, such as less than 5% by weight of the carrier) so that it does not cause undue drying of the barrier membrane.

Examples of antipsoriatic drugs or drugs for seborrheic dermatitis treatment include, but are not limited to, corticosteroids (e.g., betamethasone dipropionate, betamethasone valerate, clobetasol propionate, diflorasone diacetate, halobetasol propionate, triamcinonide, dexamethasone, fluocinonide, fluocinolone acetonide, halcinonide, triamcinolone acetate, hydrocortisone, hydrocortisone verlerate, hydrocortisone butyrate, aclometasone dipropionte, flurandrenolide, mometasone furoate, methylprednisolone acetate), methotrexate, cyclosporine, calcipotriene, anthraline, shale oil and derivatives thereof, elubiol, ketoconazole, coal tar, salicylic acid, zinc pyrithione, selenium sulfide, hydrocortisone, sulfur, menthol, and pramoxine hydrochloride, and salts and prodrugs thereof.

Examples of anti-viral agents for viral infections such as herpes and hepatitis, include, but are not limited to, imiquimod and its derivatives, podofilox, podophyllin, interferon alpha, acyclovir, famcyclovir, valcyclovir, reticulos and cidofovir, and salts and prodrugs thereof.

Examples of anti-inflammatory agent, include, but are not limited to, suitable steroidal anti-inflammatory agents such as corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and salts are prodrugs thereof. The preferred steroidal anti-inflammatory for use in the present invention is hydrocortisone. A second class of anti-inflammatory agents which is useful in the compositions of the present invention includes the nonsteroidal anti-inflammatory agents.

Other active agents include, but are not limited to, wound healing enhancing agent, such as recombinant human platelet-derived growth factor (PDGF) and other growth factors, ketanserin, iloprost, prostaglandin $E_1$ and hyaluronic acid, scar reducing agents such as mannose-6-phosphate, analgesic agents, anesthetics, hair growth enhancing agents such as minoxadil, hair growth retarding agents such as eflornithine hydrochloride, antihypertensives, drugs to treat coronary artery diseases, anticancer agents, endocrine and metabolic medication, neurologic medications, medication for cessation of chemical additions, motion sickness, protein and peptide drugs.

In one embodiment, the carrier contains a fragrance effective for reducing stress, calming, and/or affecting sleep such as lavender and chamomile.

The amount of the active agent in the carrier will depend on the active agent and/or the intended use of the device. In one embodiment, the carrier contains a safe and effective amount of the active agent, for example, from about 0.001 percent to about 20 percent, by weight, such as from about 0.01 percent to about 5 percent, by weight, of the carrier.

Light Emitting Diode

In one embodiment, the device contains one or more light emitting diodes. Light emitting diodes (LEDs) of certain spectrum may be incorporated into the device to emit light to the barrier membrane (e.g., to treat skin conditions such as acne and rosacea). The light emitting diode may also provide a signal to the user indicating that the device is operating properly.

In one embodiment, the LED is one that emits light periodically (i.e., a blinking LED). In a further embodiment, such LED also modulates the current passing through the barrier membrane to form a pulsatile DC current. Such pulsatile DC current can enhance delivery of active agents into the barrier membrane, stimulate biological responses in the barrier membrane such as enhancing wound healing (e.g., in acne lesions), and/or enhanced skin sensation which serves a signal to a user that the device is working. Another potential advantage of using a blinking LED is to produce pulsatile DC current without the need of a complex electric circuit.

The spectrum of the LED's according to the current invention may range from about 300 nm to about 1500 nm, such as from about 350 nm to about 1000 nm. In one embodiment, the range of the LED includes violet-blue, green, red, and infrared ranges, e.g., from about 400 nm to about 450 nm such as from about 407 nm to about 420 nm; from about 510 nm to about 550 nm; from about 600 nm to about 700 nm; and from about 1300 nm to about 1500 nm. In one embodiment, the device contains two LEDs, one that emits light having a wavelength of from about 400 nm to about 500 nm and one which emits light from about 700 nm to about 1000 nm. Photosensitizer agents, such as 5-aminolaevulinic acid (ALA), hypericin, St. John's wort powder or extract, or other synthetic or natural photosensitizer agents, may be incorporated into the carrier as active agents to be delivered and irradiated by the device with LED's of the present invention. The light irradiation from the LED's, together with the photosensitizer agent(s) and other aforementioned active agents, electrochemically generated oxidizing agents (e.g., peroxides, nascent oxygen, chlorine dioxide, and chlorine), and/or electric stimulation of the barrier membrane may work synergistically to achieve an improved efficacy in treating membrane disorders such as acne and rosacea.

General Use

In one embodiment, the device is used for the treatment of a barrier membrane condition (e.g., the delivery of an active agent light, and/or electricity into the membrane such as the skin, eye (cornea, retina, etc.), oral, buccal, nasal, vaginal, gastrointestinal, or rectal mucosa barrier membrane, of a human). In one embodiment, the device is used for the treatment of skin conditions. Examples of such treatments include, but are not limited to: treatment of acne, rosacea, or other microbial infections of the skin; reduction the visible signs of skin aging (e.g., wrinkles, sagging, and age-spots); folliculitis and pseudo-folliculitis barbae; treatment of wounds and lesions (e.g., enhancing healing and scar reduction); sebum regulations (e.g., sebum reduction or oily/shining skin appearance inhibition or control); pigmentation regulation (e.g., reduction of hyperpigmentation or pigmentation of light skin); hair growth retardation (e.g., skin on the leg) or hair stimulation (e.g., scalp); and treatment of dermatitis (e.g., atopic, contact, or seborrheic dermatitis) and/or psoriasis.

In another embodiment, the device is used for the treatment of mucosal conditions (e.g., mucosa in the oral or vaginal cavities). Examples of such treatments include, but are not limited to: treatment of vaginal candidiasis and vaginosis, genital and oral herpes, cold sore, canker sore, oral hygiene, periodontal disease, and other microbial infections of the mucosa.

Another embodiment of the present invention is the device induces certain desirable biological responses that facilitate the treatment of the barrier membrane conditions. These desirable biological responses may be induced by the electric current passage through the barrier membrane, and/or the electrochemically generated oxidizing materials, together with the active agents delivered by iontophoresis from the carrier, in treating the barrier conditions. Examples of the desirable responses of the barrier membrane may include, but are not limited to, sebum regulation (e.g., reduction of sebaceous gland activity), inhibition of anaerobotic microbial growth and establishment of a healthier membrane microflora or (e.g, reduction of *P. acne* growth and of production of irritating fatty acids), blood vasoconstriction (thus promoting local accumulation of active agents or removal of dark circle under the eye due to deoxyhemoglobins), enhanced tissue immunological activity (e.g, increased elimination of pathogenic microbes on tissue's own defense systems), improved tissue repairing (e.g., enhanced healing and reduced scarring of lesions such as acne lesions), and improved keratolytic activity of the carrier (e.g., softening of keratin plugs of comedos in whiteheads and blackheads of acne, and facilitating their removal).

In another aspect, the invention also features the method of converting an active agent from a less active form to a more active form via oxidation or reduction via an inert electrode (e.g., cystine to cysteine, disulfide acetyl-cysteine to acetyl-cysteine, and retinol to retinoic acid). Thus, an unstable agent can be stored in a more stable form and converted to its active form prior to administration. In a further aspect, the generation of reducing agents by the device of the present invention can be used to stabilize oxygen-labile active agents. Examples of such oxygen-labile active agents include, but are not limited to, retinoids, ascorbic acid, and benzoyl peroxide.

In one embodiment, the invention also features the method of converting an active agent from a less active form to a more active form via oxidation at an reactive anode, such as an anode made of zinc, magnesium, copper, aluminum, alloy or mixture of these metals. For example, an anode made of zinc releases zinc ions with the passage of an electric current through the electrode. The zinc ions generated by such an electrochemical reactions are then subsequently delivered by the electric repulsion of the positively charged anode into the barrier membrane. In one embodiment, such ions are deposited into the hair follicles and/or sebaceous glands to inhibit *P. acnes* growth and/or suppress skin tissue inflammation resulted from *P. acnes* over growth before the treatment. Similarly, a zinc-copper alloy anode or another zinc-beneficial metal alloy releases both zinc ions and copper ions or the other beneficial ions, respecyytively, into the hair follicles and sebaceous glands for acne treatment and prevention.

Skin Conditions

In one embodiment, the device of the present invention is used to treat skin conditions such as: acne and acne (e.g., blackheads and whiteheads) and acne-related skin conditions such as rosacea and nodule-cystic; hyperpigmentation such as freckles, melasma, actinic and senile lentigines, age-spots, post-inflammatory hypermelanosis, Becker's naevus, dark circles under the eye, and facial melanosis; stretch marks; and skin aging effects on the skin (such as those caused by photodamage) including wrinkling, roughness, pigmentary alterations, sallowness, fine lines, and laxity, by delivering active agents that including pre-formulated active agents in the carrier and electrochemically generated active agents (e.g., beneficial metal ions) by the electrodes, and/or by providing electric stimulation to the skin tissues.

In one embodiment, the device of the present invention provide multiple mechanism of actions to treat such conditions: namely, (a) target—delivering pre-formulated active agents into the pilosebaceous unit by iontophoresis and electro-osmosis; (b) electrochemically generating new active agents (e.g., the beneficial metal ions from a reactive anode) and targeted delivery of the freshly generated active agents to the pilosebaceous unit (e.g., beneficial ions such as zinc and copper have known to enhance skin's own immune system); and/or (c) providing electric stimulation to the pilosebaceous unit and its surrounding skin tissues to increase blood circulation, and to treat the skin by reducing inflammation, enhancing wound healing, and/or increasing skin exfoliation.

Wounds and Scars

In one embodiment, the device of the present invention can be incorporated into wound dressings and bandages to provide electric therapy for healing enhancement and scar prenvetion. In one embodiment, the wound exudation fluid and/or wound cleansing solution serves to activate a galvanic wound dressing/bandage to deliver active agents pre-incorporated in the wound dressing/bandage and/or to generate electrochemically beneficial metal ions followed with delivery of the beneficial metal ions into the wound. The device also treats the wound with therapeutic electric current which may increase blood circulation, stimulate tissue immune response, and/or suppress tissue inflammation, which may lead to accelerated healing and reduced scarring.

Enhanced Chemical Peel

Chemical peel treatments are an in-office procedure that involves the application of a chemical agent to the skin to induce controlled destruction or exfoliation of old skin and stimulation of new epidermal growth with more evenly distributed melanin. When peel agents reach the dermal layer, important wound-healing activities occur that cause skin remodeling and skin smoothing, both are anti-aging benefits. Delivery of chemical peel agents contained with the carrier of electrical generating device/composition could be used in the treatments for a variety of skin disorders, including but not limiting to, acne, post-inflammatory hyperpigmentation, melasma, scar, photo-damage, age-spot, wrinkle, stretch mark, birth mark, uneven texture and tone, warts, and pseudo-folliculitis barbae. The device/composition may also have the additional advantage of reducing skin irritation and decreasing the risk of precancerous and early cancerous lesions of the photo-aged skin on the face, because the iontophoretically administrated chemical peel may enable the use of a much lower concentration of chemical peeling agents in comparison to the standard chemical peel approach without the use of such device. Reduction of required chemical peeling agents may also minimize risk of prolonged post-peel erythema, inflammation and scars from chemical peel while achieving desirable benefits.

Examples of chemical peel agents include, but are not limited to: hydoxy acids such as α-hydroxy acids such as lactic acid, malic acid, glycolic acid, arginine glycolate, ammonium glycolate and sodium glycolate; β-hydroxy acids such as salicylic acid; polyhydroxy acids (PHA) such as gluconolactone; and non-hydroxy acids such as acetic acid, trichloroacetic acid (TCA), pyruvic acid an alpha-keto-acid, phenol, their derivatives or their combinations. They can also be combined with sulfur, resorcinol, retinoids or other active actives such as Jessner solution peel (which contains lactic acid, salicylic acid, resorcinol and ethyl alcohol). Chemical peeling agents of the present invention may also include, but are not limited, protease agents or their derivatives such as acid protease in the apoenzyme, holoenzyme, idoenzyme, or zymogen form. Examples include pepsin, Bromelain, papaya, and cathepsin. Further examples include natural extract chemical peeling agents such as fruit extracts, mushroom extract, and other plant extracts.

In one embodiment, the duration of the application of the device to the skin is from about 2 to about 10 minutes depending on the individual skin conditions. In one embodiment, the carrier contains from about 0.1% to about 70% by weight of such chemical peel agent, such as from about 0.5% to about 20% such as from about 2% to about 10%.

Shape

The device includes a housing that may be fabricated into various shapes and sizes to fit the contours of various anatomical surfaces of the barrier membranes. For examples, the housing may be a substrate made in the shape of a whole facial mask with openings/holes to expose the eyes, eye bows, nose, and mouth; a partial facial mask covering only the upper or lower half of the face; or a patch covering only the forehead, or the under eye region, the chin and jaw region, the neck, the back, wound, acne lesion or pimple, or other specific area of a barrier membrane in need of treatment.

In one embodiment of the present invention, the housing is a water-insoluble substrate containing a galvanic couple, for example, a fine zinc wire or a fine zinc-coated fiber (e.g., zinc-coated polymer fiber) connected to a fine copper wire or a fine copper-coated fiber (e.g., copper-coated polymer fiber). One or more such fine galvanic couple wire(s) or fiber(s) may be incorporated into the substrate to create a device which, when in contact with the carrier (such as tap water or a liquid or semi-liquid composition including active agents) generates an electric current. In one embodiment, a galvanic couple-containing substrate may be made of multiple layer, for example, a layer of the zinc-containing substrate (e.g., a fine zinc wire- or a fine zinc-coated fiber in a woven or non-woven fabric) over a layer of copper-containing substrate (e.g., a fine copper wire- or a fine copper-coated fiber in a woven or non-woven fabric). During use, the layers contact each other to form the galvanic couple. In a further embodiment, the device releases beneficial ions (e.g., zinc ions or aluminum ions) that are delivered to the barrier membrane (e.g., the skin) when such a substrate is applied by the user (e.g., used as a wipe for cleaning the skin or a facial patch or mask to treat the skin). Active agents may also be incorporated into the substrate during manufacturing processes or be subsequently applied to the substarte prior to the application to the barrier membrane (e.g., in the form of an electrolyte or active agent containing liquid spray to wet the substrate). In one embodiment, the fabric is used as a dry wipe or a dry full or partial facial mask, to be wetted immediately before use, by applying water to the dry wipe or facial mask to pre-moisturized skin (e.g., by washing with tap water).

By "water insoluble" is meant that the substrate, upon immersion in distilled water at 25° C., does not readily dissolve in or readily break apart. The water-insoluble substrate may, however, be disintegrated and/or dissolved slowly, i.e., over a period of several hours up to several days. A wide variety of materials can be used as the water-insoluble substrate. Examples of suitable substrates include, but are not limited to, non-woven substrates, woven substrates, hydroentangled substrates, air entangled substrates, natural sponges, synthetic sponges, and polymeric netted meshes.

The water insoluble substrates may be flushable. As used herein, by "flushable" is meant that the substrate will pass through at least 10 feet of waste pipe in two toilet flushes. The material may also be biodegradable.

In one embodiment, the substrates contain a non-woven material. By "non-woven" is meant that the substrate, or a layer of the substrate, is comprised of fibers that are not woven into a fabric but rather are formed into a sheet, mat, or pad layer. The fibers can either be random (i.e., randomly aligned) or they can be carded (i.e., combed to be oriented in primarily one direction. Furthermore, the non-woven substrate can be composed of a combination of layers of random and carded fibers).

Non-woven substrates may be comprised of a variety of natural and/or synthetic materials. By "natural" is meant that the materials are derived from plants, animals, insects, or byproducts of plants, animals, and insects. By "synthetic" is meant that the materials are obtained primarily from various man-made materials or from natural materials, which have been further altered. Non-limiting examples of natural materials useful in the present invention are silk fibers, keratin fibers (such as wool fibers, camel hair fibers) and cellulosic fibers (such as wood pulp fibers, cotton fibers, hemp fibers, jute fibers, and flax fibers).

Examples of synthetic materials include, but are not limited to, those selected from the group containing acetate fibers, acrylic fibers, cellulose ester fibers, cotton fibers, modacrylic fibers, polyamide fibers, polyester fibers, polyolefin fibers, polyvinyl alcohol fibers, rayon fibers, polyurethane foam, and mixtures thereof.

Substrates made from one ore more of the natural and synthetic materials useful in the present invention can be obtained from a wide variety of commercial sources such as Freudenberg & Co. (Durham, N.C. USA), BBA Nonwovens (Nashville, Tenn. USA), PGI Nonwovens (North Charleston, S.C. USA), Buckeye Technologies/Walkisoft (Memphis, Tenn. USA), and Fort James Corporation (Deerfield, Ill. USA).

Methods of making non-woven substrates are also well known in the art. Such methods include, but are not limited to, air-laying, water-laying, melt-blowing, spin-bonding, or carding processes. The resulting substrate, regardless of its method of production or composition, is then subjected to at least one of several types of bonding operations to anchor the individual fibers together to form a self-sustaining web. The non-woven substrate can be prepared by a variety of processes including hydro-entanglement, thermally bonding, and combinations of these processes. Moreover, the substrates can have a single layer or multiple layers. In addition, a multi-layered substrate can include film layer(s) (e.g., aperture or non-aperture film layers) and other non-fibrous materials.

Strength or firmness of the non-woven material may be a desirable attribute. This can be achieved, for example, by the addition of binding materials, such as wet strength resins, or the material may be made of polymer binder coatings, stable fibres, e.g. based on cotton, wool, linen and the like. Examples of wet strength resins include, but are not limited to, vinyl acetate-ethylene (VAE) and ethylene-vinyl chloride (EVCL) Airflex emulsions (Air Products, Lehigh, Pa.), Flexbond acrylic polymers (Air Products, Lehigh, Pa.), Rhoplex ST-954 acrylic binder (Rohm and Haas, Philadelphia, Pa.), and Ethylene-vinyl acetate (EVA) emulsion (DUR-O-SET® by National Starch Chemicals, Bridgewater, N.J.). The amount of binding material in the substrate may range from about 5% to about 20%, by weight, of the substrate.

Non-woven materials of increased strength can also be obtained by using the so-called spunlace or hydro-entanglement technique. In this technique, the individual fibers are twisted together so that an acceptable strength or firmness is obtained without the need to use binding materials. The advantage of the latter technique is the excellent softness of the non-woven material.

In one embodiment, the non-woven material is made of a superabsorbent polymer. For the purposes of the present invention, the term "superabsorbent polymer" refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and other material known to the art of absorbent article manufacture.

Additives may also be added in order to increase the softness of the substrates. Examples of such additives include, but are not limited to, polyols such as glycerol, propylene glycol and polyethylene glycol, phthalate derivatives, citric esters, surfactants such as polyoxyethylene (20) sorbitan esters, and acetylated monoglycerides.

Sensory attributes may also be incorporated to the insoluble non-woven substrates. Examples of such sensory attributes include, but are not limited to color, texture, pattern, and embossing.

In one embodiment, the device of the present invention is for use as a wipe or towel (for example, having a surface area of from about 20 $cm^2$ to about 10,000 $cm^2$). In another embodiment, the device of the present invention is for use as a therapeutic patch or mask for application to a portion of or substantially all of the face (for example, having a surface area of from about 1 $cm^2$ to about 600 $cm^2$)

In one embodiment, the carrier is present in at least about 50%, such as at least about 75%, by weight of the total weight of the water insoluble substrate prior to use. In another embodiment, (i) the liquid carrier is present in less than about 10%, such as less than about 1%, by weight of the total weight of the water insoluble substrate (for example, the device may not contain any carrier prior to use). In a further embodiment, the product contains instructions for the user to either (i) wet the substrate prior to application or (ii) wet the barrier membrane (e.g., the skin) with water and/or another liquid prior to application.

Devices

One embodiment of the present invention is represented schematically in FIG. 1. The device 500 contains a removable release liner 100, a carrier layer 120, a first conductive electrode 140, a second conductive electrode 240, electric lead wires 110 and 210 connecting the two ends of an electrically insulated connecting wire 350 to the two dissimilar conductive electrodes, an optional electric power switch 330 located on the lead wire 210, a backing layer 160, and a cover layer 340.

The gap "b" depicts the distance between two conductive electrodes 140 and 240 to the release liner (or the membrane following application of the device), and the gap "a" represents the distance between two oppositely charged conductive electrodes. In one embodiment, gap "a" is between 0 to about 20 centimeter, and gap "b" is between 0 and to about 1 centimeters. In another embodiment, the ratio of gap "a" to gap "b" is from about 0 to about 20.

In devices that contain a battery as a power source, electrically insulated connecting wire 350 can be replaced with a battery (not shown) in the Figures. The battery may be encased in an electric insulating, water-impermeable polymer layer (not shown in the Figures). Optionally, there can be an electric circuit (not shown) in device 500 to provide a constant current located between the battery (not shown) and conductive electrode 140 and/or conductive electrode 240.

When a zinc air battery is used as the power source of the device 500, the battery (not shown) is constructed in such a way that the orifice on the stainless steel cover is facing the opposite side of the carrier layer 120. An orifice is made on the battery cover layer to expose the orifice on the zinc air battery that is covered by a removable oxygen-impermeable cover. In this case, the power switch 330 is replaced by the removable oxygen-impermeable cover. The removable oxygen-impermeable cover can be used to begin (by removing it) or to halt the electrotransport process of the device (by re-covering the orifice).

The backing layer 160 may be impermeable to the active agent contained within the carrier layer 120, and is preferably not permeable to water or other solvents in the carrier layer 120. The backing layer 160 and cover layer 340 may be made of flexible material that is impermeable to water and electrically insulating, e.g., polymers such as polyethylene, polypropylene, polyvinyl acetate, polyurethane, silicone rubber, or polyvinyl chloride.

In a further embodiment, the backing layer 160 is permeable to electrochemically generated gases (e.g., oxygen, chlorine, and hydrogen) in order to limit excess accumulation of the gases in the carrier which can cause tissue irritation and/or undesirable deformation of the device. Examples of such "breathable backing" material include, but are not limited to, a cotton or synthetic woven and nonwoven fabric layer, such as those fabric materials commonly used for bandages and sports bandages.

The carrier layer 120 is an adhesive hydrogel containing the active agent. The active agent may be incorporated into the carrier layer 120 as dissolved molecules and ions, dispersed solid particles, or liquid droplets such as cream, lotion, emulsion, multi-emulsion, microemulsion, and/or liposome compositions. The carrier layer 120 may also contain a solid supporting matrix (e.g., a gauze, non-woven or sponge-like material).

A removable liner sheet 100 covers the carrier layer 120. The selection of the removable release-liner 100 is dependent on the type of the adhesive hydrogel used in carrier layer 120. The release liner sheet 100 is typically a polymer sheet or a paper or fabric coated with a polymer, which has weak adhesion toward the adhesive hydrogel layer 120, thereby allowing it to be easily removed from the carrier layer 120 prior to use without damaging the carrier layer 120. Examples of the polymers typically used for the release liner 100 are silicones and polyethylenes. Alternatively, a wax may be used in the place of the polymer to coat the release liner 100.

In addition to, or in lieu of, the use of an adhesive in the carrier layer 120, the device 500 may be fastened to the barrier membrane with an adhesive tape, an elastic band, a band with a buckle (similar to a leather watch band), or a Velcro® band.

In order to use device 500, the removable release liner sheet 100 is peeled off, and the carrier hydrogel layer 120 of the device 500 is affixed to a barrier membrane, such as the skin or mucosal membranes such as vaginal, oral, buccal, nasal, gastrointestinal or rectal mucosa barrier membrane, of the user. The device may be directly affixed to the barrier membrane if the carrier layer 120 contains an adhesive hydrogel. An electric potential is applied across the conductive electrodes 140 and 240 by switching on the power switch 330.

Figure 2:
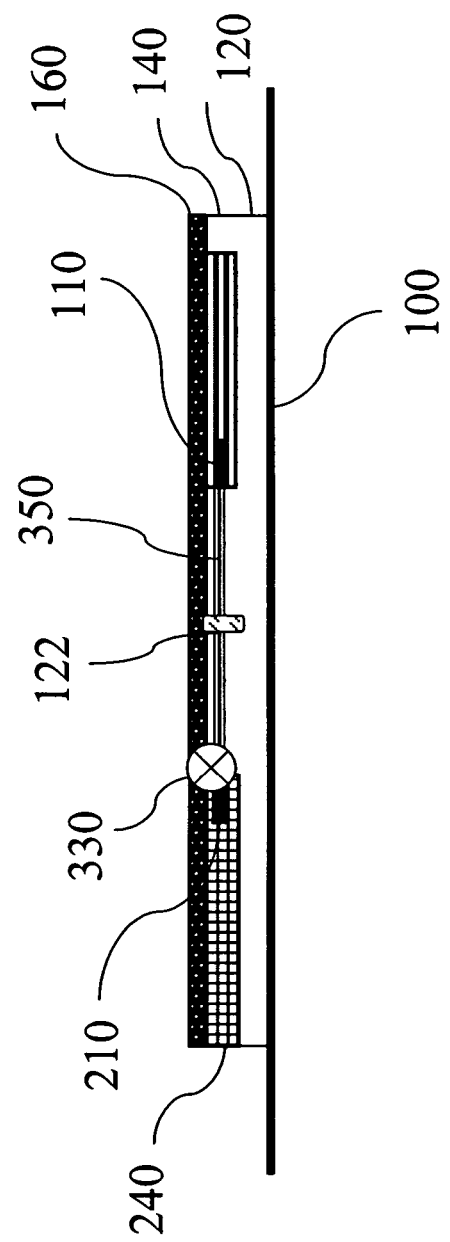
FIG. 2 is a cross-sectional view of one embodiment of the device suitable for practicing the invention. The conductive electrodes 140 and 240 are connected respectively by the lead wires 110 and 210 to electrically insulated connecting wire 350 embedded in the carrier layer 120 of the device 500.

Another embodiment of the present invention is represented schematically in FIG. 2. The electrically insulated connecting wire 350 is located within the carrier layer 120. The advantage of this arrangement includes reduced bulkiness, enhanced esthetics and user comfort.

The lighting portion of the LED 122 is preferable located in the carrier layer 120 in close proximity to the skin. Locating the light source in the carrier layer 120 affixed to the barrier membrane has an advantage of minimizing the loss of light energy from reflection of skin surface. In addition, a light reflective layer may be used as the backing layer 160 (e.g., metalized polymer film) to further enhance the efficacy of phototherapy, and to achieve more homogeneous irradiation. The backing layer 160 may optionally be perforated as certain spots to make the light visible to the user to serve as an indicator that the device is working normally.

Figure 3:
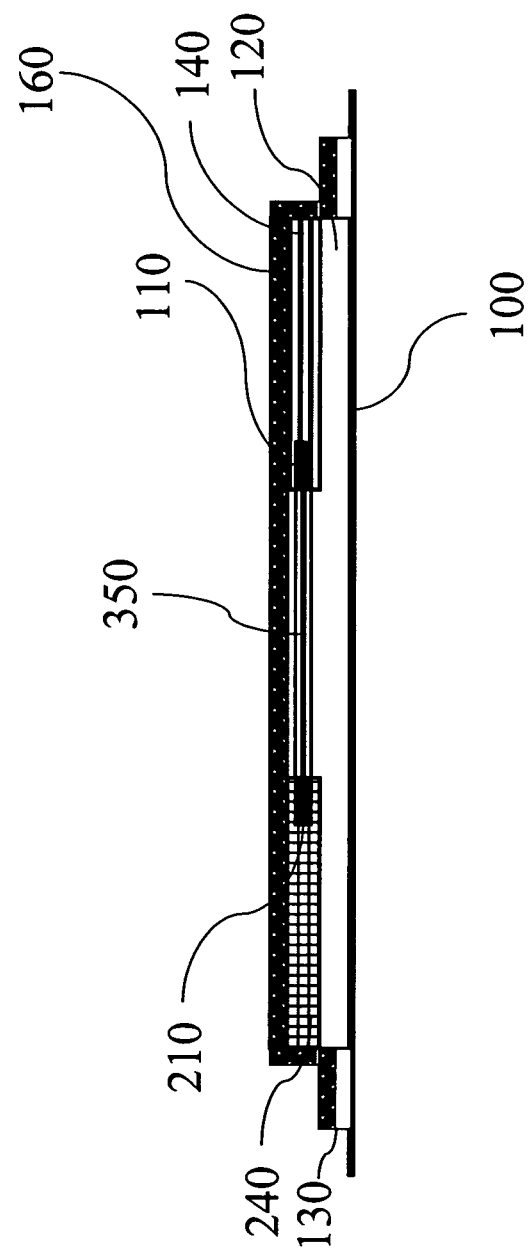
FIG. 3 is a cross-sectional view of one embodiment of the device suitable for practicing the invention. The conductive electrodes 140 and 240 are connected respectively by the lead wires 110 and 210 to electrically insulated connecting wire 350 embedded in the carrier layer 120.

Another embodiment of the present invention is represented schematically in FIG. 3. Backing layer 160 (e.g., the housing) contains an adhesive layer 130 coated onto the outer rim of the backing layer 160 for affixing device 500 to membrane during application. The adhesive in the adhesive layer 130 may be a polymeric, pressure sensitive and/or nonconductive. Suitable adhesive materials include, but are not limited to, silicones, polyisobutylenes and derivatives thereof, acrylics, natural rubbers, and combinations thereof. Suitable silicone adhesives include, but are not limited to, Dow Corning 355 (available from Dow Corning of Midland, Mich.); Dow Corning X7-2920; Dow Corning 0 X7-2960; GE 6574 (available from General Electric Company of Waterford, N.Y.); and silicone pressure sensitive adhesives. Suitable acrylic adhesives include, but are not limited to, vinyl acetate-acrylate multipolymers, including, such as Gelva-7371 (available from Monsanto Company of St. Louis, Mo.); Gelva T 7881; Gelvac 2943; 1-780 medical grade adhesive available from Avery Dennison of Painesville, Ohio; and acrylic pressure sensitive adhesives.

One embodiment of the present invention is a dual-pack system, in which the device and the carrier (or a portion of the carrier) are packaged separately. One portion of the carrier layer 120 may be an anhydrous liquid-immobilizing matrix, such as a dry woven or nonwoven fabric, a sponge, or a dehydrated hydrogel layer (e.g., freez-dried hydrogel), while the liquid portion of the carrier, such as a solution, gel, or cream containing active agents, is packaged in a separate liquid containing compartment (not shown in the Figures), such as a unit dose pouch, a breakable container or a bottle. Prior to use, the liquid-containing compartment is broken and the liquid or semisolid portion of the carrier is applied to the liquid-immobilizing matrix to activate the current generation for skin application. The active agents are either incorporated into the liquid-immobilizing matrix or the liquid/semisolid composition.

Figure 4:
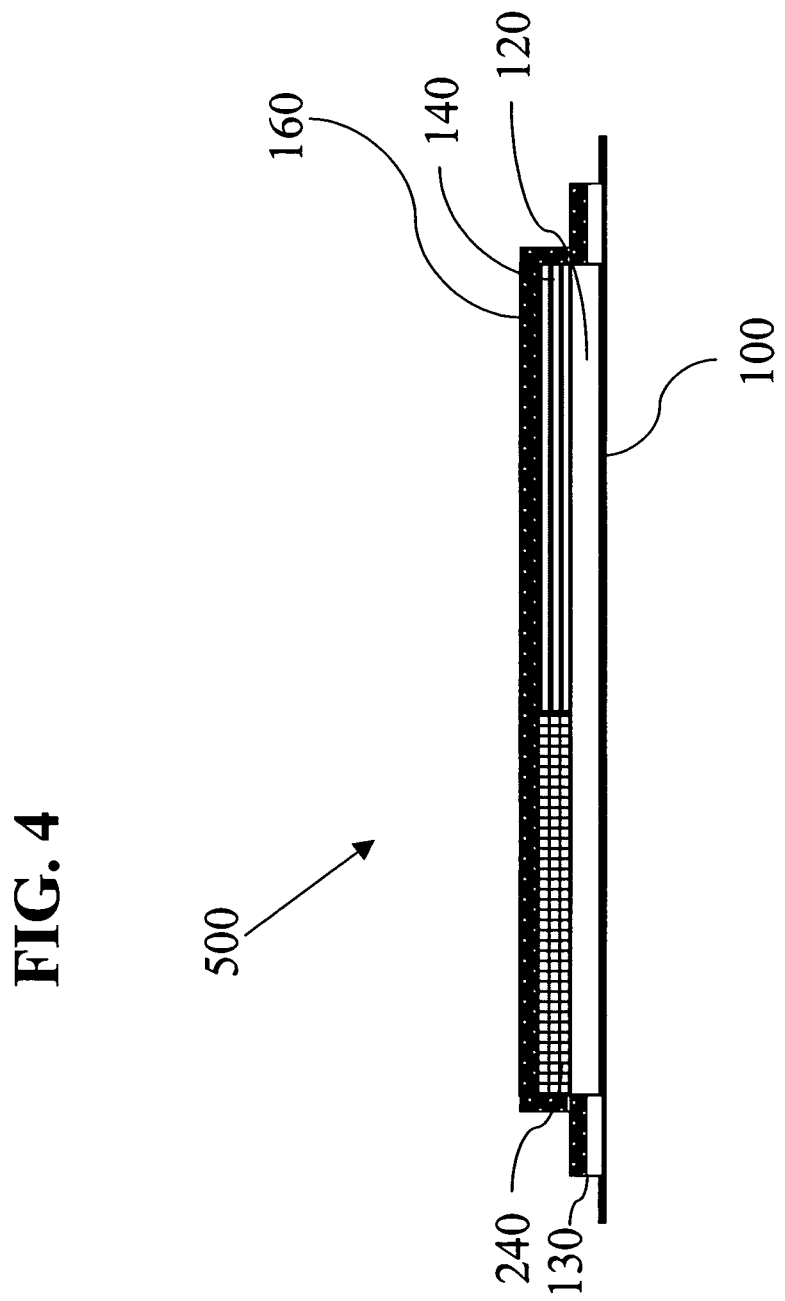
FIG. 4 is a cross-sectional view of one embodiment of the device suitable for practicing the invention. The conductive electrodes 140 and 240 are in electric communication with each other by direct connection.

One embodiment of the present invention is represented schematically in FIG. 4. The conductive electrodes 140 and 240 is in electric communication with each other through direct connection, namely, the gap "a" (the distance between two oppositely charged conductive electrodes) is equal to zero. Two conductive electrodes forms a galvanic couple which is contact the carrier layer 120 enclosed in backing layer 160 with an opening affixed to the release liner 100 with an adhesive layer 130. One major advantage of this configuration is its simplicity and easiness to manufacture.

Figure 5:
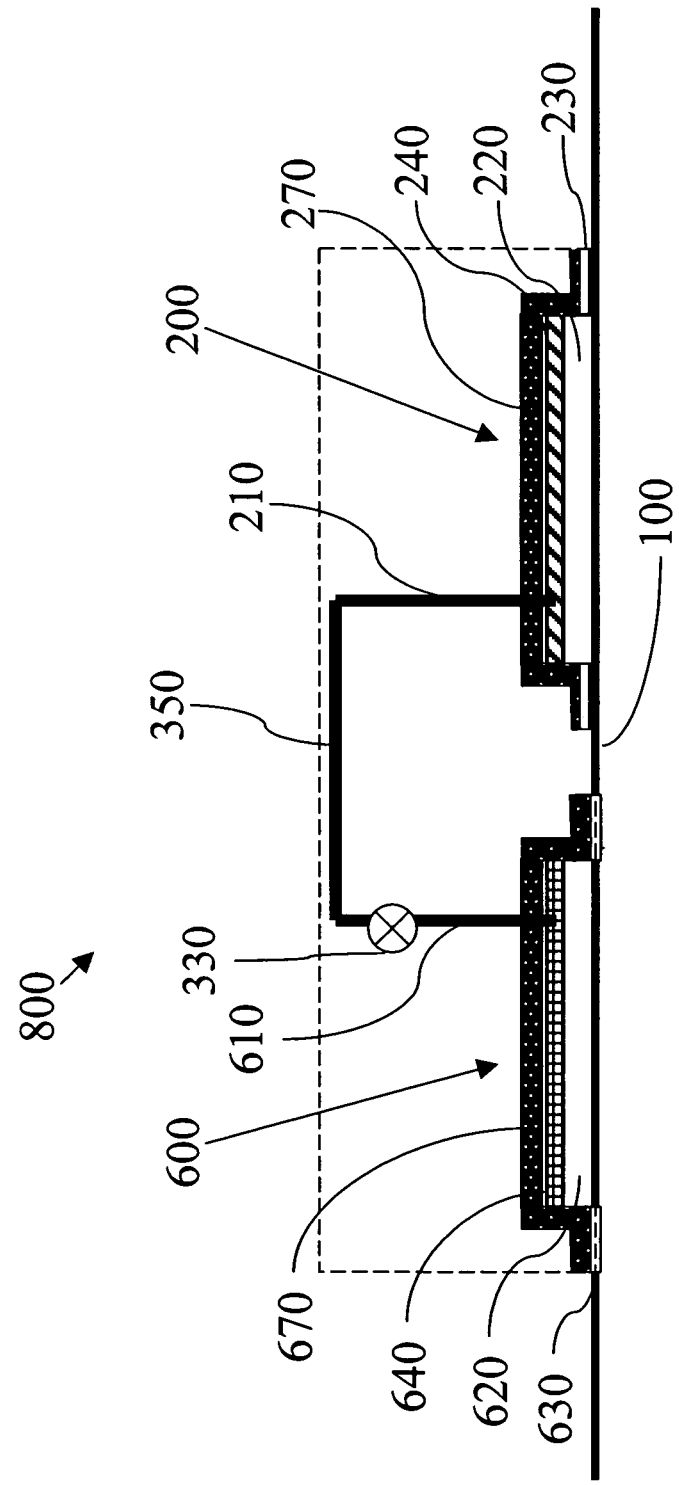
FIG. 5 is a cross-sectional view of one embodiment in accordance with the invention. The device 800 contains two electrode assemblies 200 and 600.

Another embodiment of the present invention is represented schematically in FIG. 5. The electrotransport device 800 contains two electrode assemblies 200 and 600, respective adhesive layers 230 and 630, respective carrier layers 220 and 620, respective conductive electrodes 240 and 640, respective backing layers 270 and 670, respective electric leads 210 and 610, electrically insulated connecting wire 350 and optional electric switch 330. Similar to the aforementioned typical iontophoresis device, the two electrode assemblies 200 and 600 are to be affixed to the barrier membrane apart from each other, after the release liner 100 is removed prior to use.

In one embodiment, the carrier layer 120 contains at least two active agents carrying opposite electric charges. One example of such a composition is a composition containing from about 0.5 to about 2% of salicylic acid and from about 0.01 to about 0.2% of a cationic quaternary ammonium antimicrobial agents (such as benzalkonium chloride, benzethonium chloride, methyl benzethonium chloride, and cetylpyridinium chloride), phenol, and/or chlorhexidine gluconate. The device 500 of the present invention can simultaneously deliver both active agents of opposite charges into the membrane.

Figure 6:
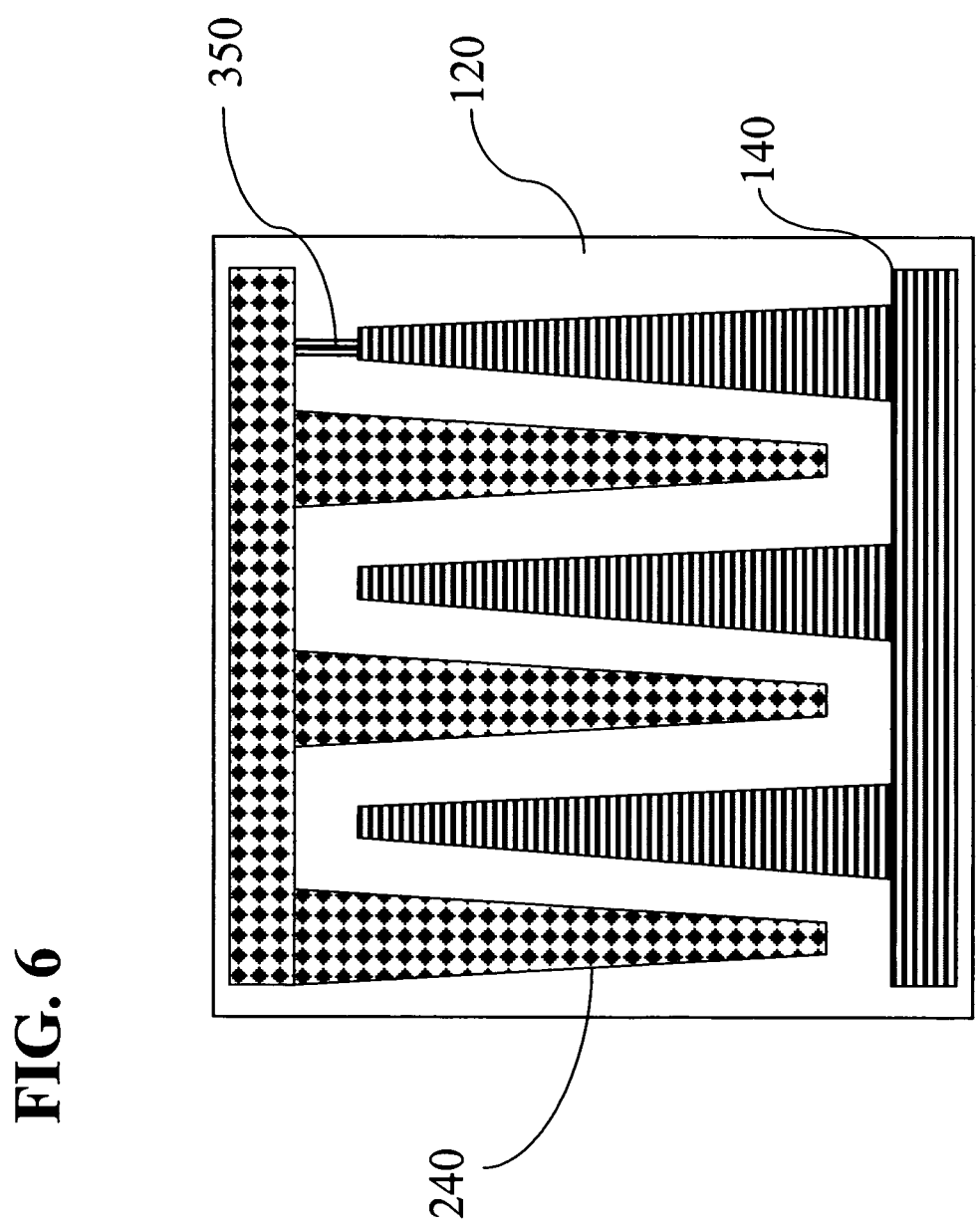
FIG. 6 is a top view of one embodiment in accordance with the invention showing the conductive electrodes 140 and 240 connected by electrically insulated connecting wire 350 embedded in the carrier layer 120. The conductive electrodes 140 and 240 are arranged in an inter-digitated configuration.
Figure 7:
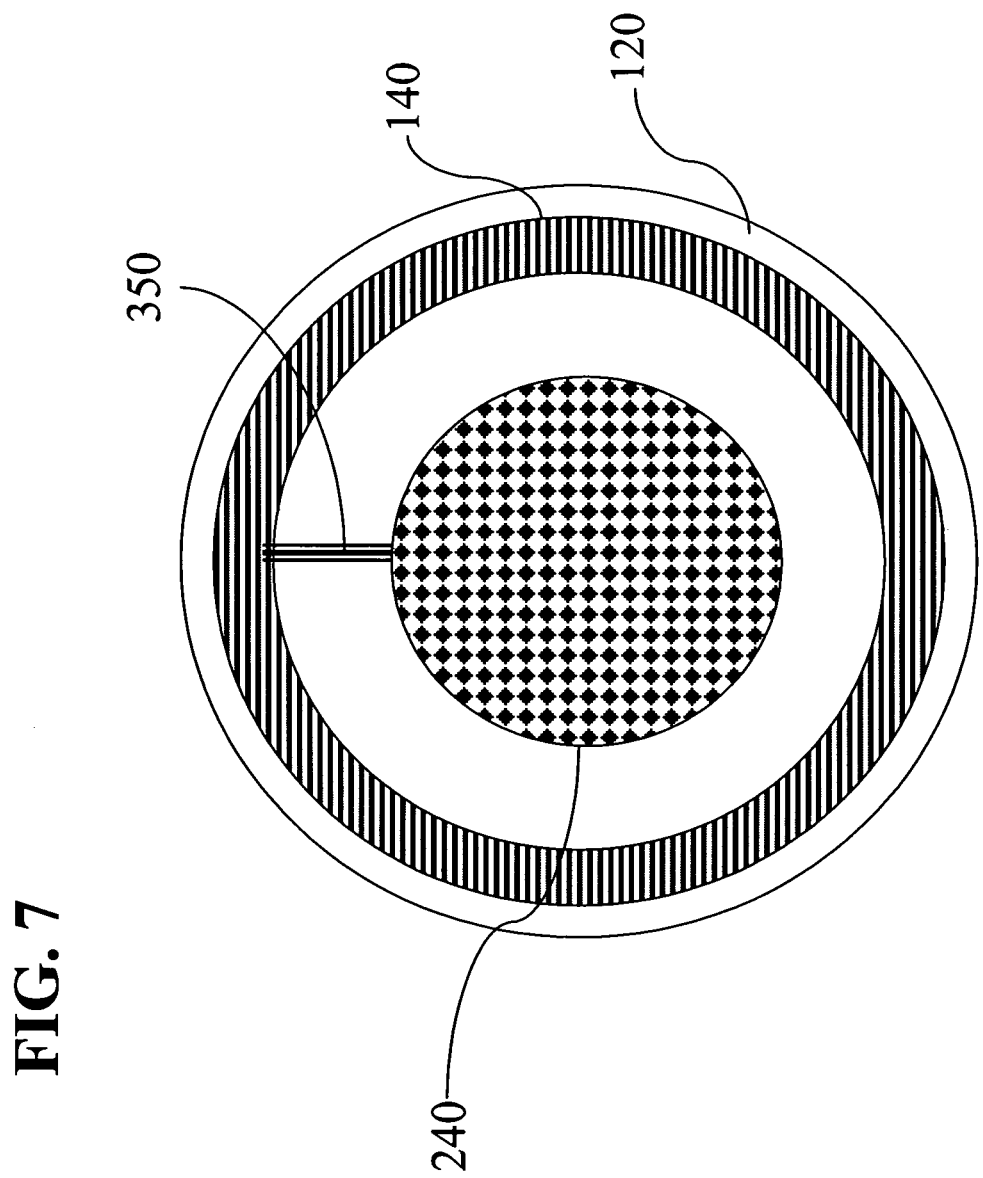
FIG. 7 is a top view of one embodiment in accordance with the invention showing the conductive electrodes 140 and 240 connected by electrically insulated connecting wire 350 embedded in the carrier layer 120. The conductive electrodes 140 and 240 are arranged in a concentric configuration.

FIGS. 6 and 7 show two examples of different configurations of dissimilar conductive electrodes 140 (shown by a double line) and 240 (shown by a single line) in carrier layer 120, connected by electrically insulated wires 350 (shown by a triple line) to form a galvanic couple power source. FIG. 6 shows that the conductive electrodes 140 and 240 are arranged in an inter-digitated configuration. FIG. 7 shows the conductive electrodes in a concentric configuration.

Figure 8:
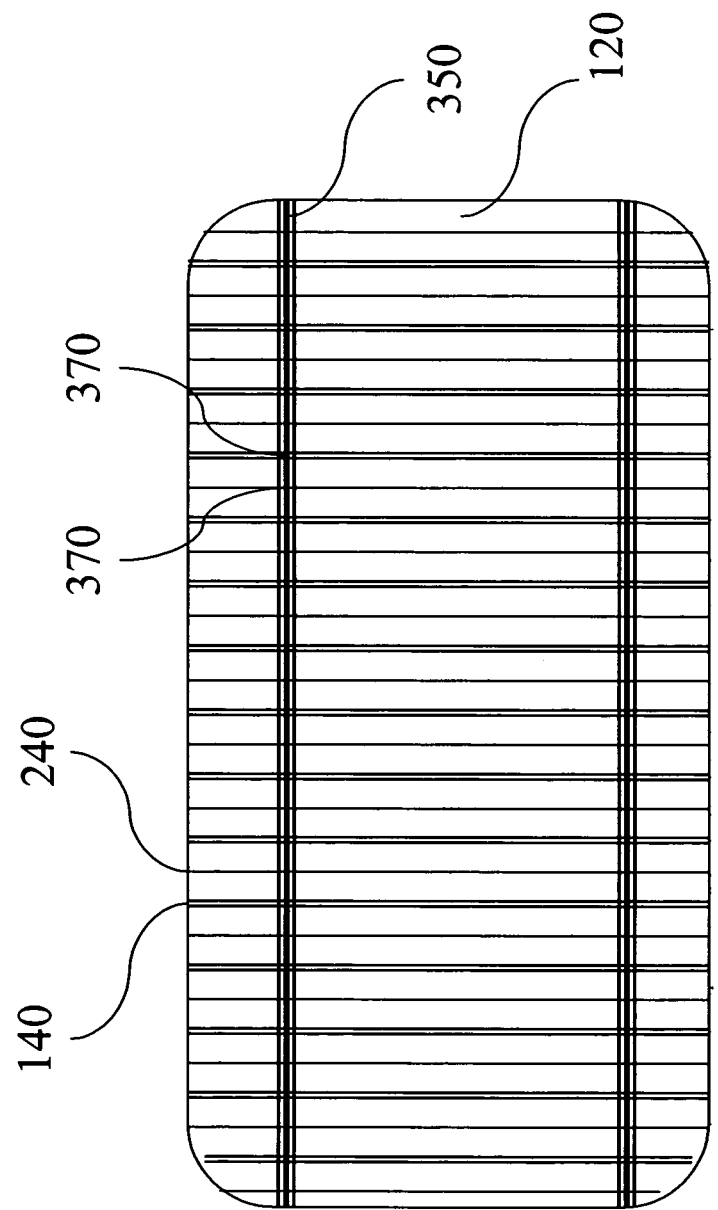
FIG. 8 is a top view of one embodiment in accordance with the invention showing a plurality of sets of conductive electrodes 140 and 240 connected to each other by connecting wire 350 to form a plurality of galvanic couple power sources, which are in contact with the carrier layer 120. The conductive electrodes 140 and 240 are arranged in a parallel configuration.
Figure 9:
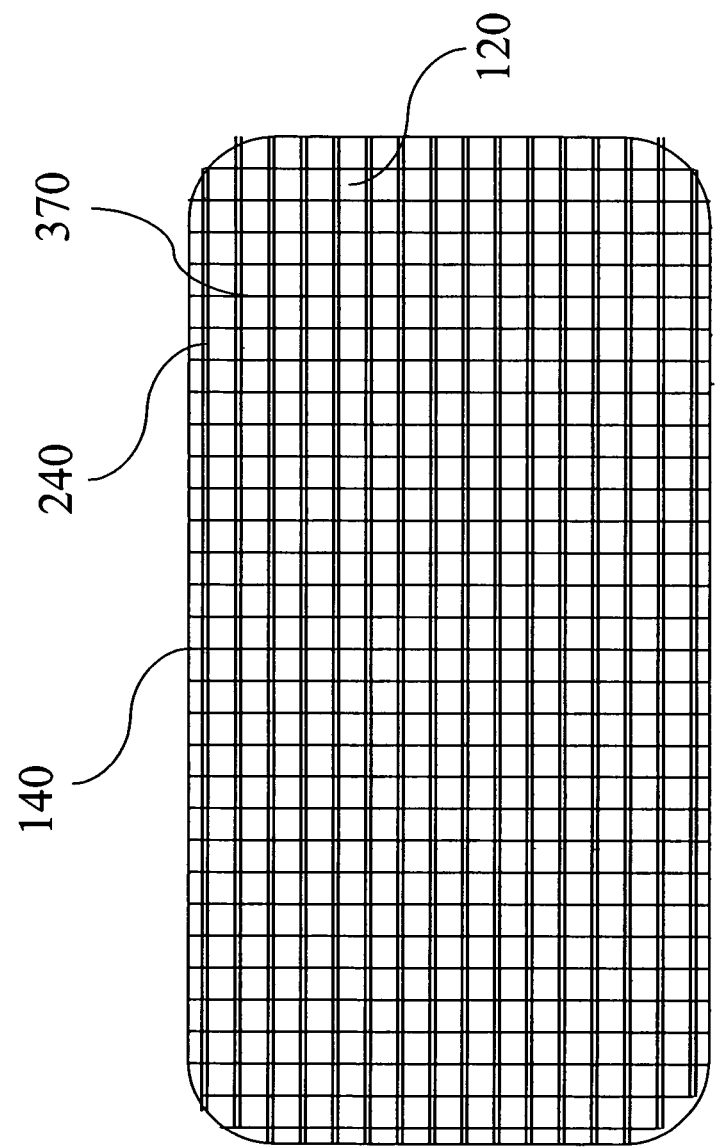
FIG. 9 is a top view of one embodiment in accordance with the invention showing a plurality of sets of conductive electrodes 140 and 240 connected to each other by a direct physical contact at intersections 370 to form a plurality of galvanic couple power sources, which are in contact with the carrier layer 120. The conductive electrodes 140 and 240 are arranged in a perpendicular configuration.

FIGS. 8 and 9 show two examples of other configurations of dissimilar conductive electrodes 140 and 240 in carrier layer 120, connected to each other either connective wire 350 as in FIG. 8 or by a direct physical contact at each intersection 370 as in FIG. 9 to form a plural of galvanic couple power sources, which are in contact with the carrier layer 120. The conductive electrodes 140 and 240 in FIGS. 8 and 9 are arranged in parallel and perpendicular configurations, respectively.

The alternating-parallel arrangement of the conductive electrodes 140 and 240 in FIG. 8 provides a more uniform electric current distribution throughout the carrier layer 120 and the underlying skin tissue, and consequently, assist in enabling a more uniform delivery of active agents into the skin. One exemplifying fabrication method for the galvanic device shown in FIG. 8 is by weaving a silver-coated polymer fabric and zinc-coated polymer fabric (or zinc wire) into a liquid-absorbant fabric layer according to the parallel electrode pattern, then connecting zinc and silver electrodes by printing over the silver and zinc regions with an electric conductive ink (e.g., conductive silver or carbon ink). Covering another layer of an electric insulating ink over the electric conductive ink will produce the electrically insulated connecting wire 350.

Another fabrication method for the device of FIG. 8 is via printing: to print onto a non-conductive polymeric substrate layer (e.g., the polymer material made of the backing layer 160) using a conductive silver or silver-silver chloride ink to produce the first conductive electrode; and to print the second conductive electrode using a conductive zinc ink. The two dissimilar conductive electrodes are then connected by printing cross them with either the conductive silver or zinc ink (or a different conductive ink such as carbon ink). A covering ink may then optionally be printed over the connecting wire to produce an electric insulating polymer layer over it. If the device is made without insulating with an electrically insulating coverying layer, the resulting device is a variation of that depicted in FIG. 9.

FIG. 9 is a top view of one embodiment in accordance with the invention showing the conductive electrodes 140 and 240 connected to each other by direct physical contact at the intersections 370 to form a galvanic couple power source, which is in contact with the carrier layer 120. The conductive electrodes 140 and 240 are arranged in a perpendicular configuration. The aforementioned fabrication methods for the device in FIG. 8 is also suitable to produce this device.

Figure 10:
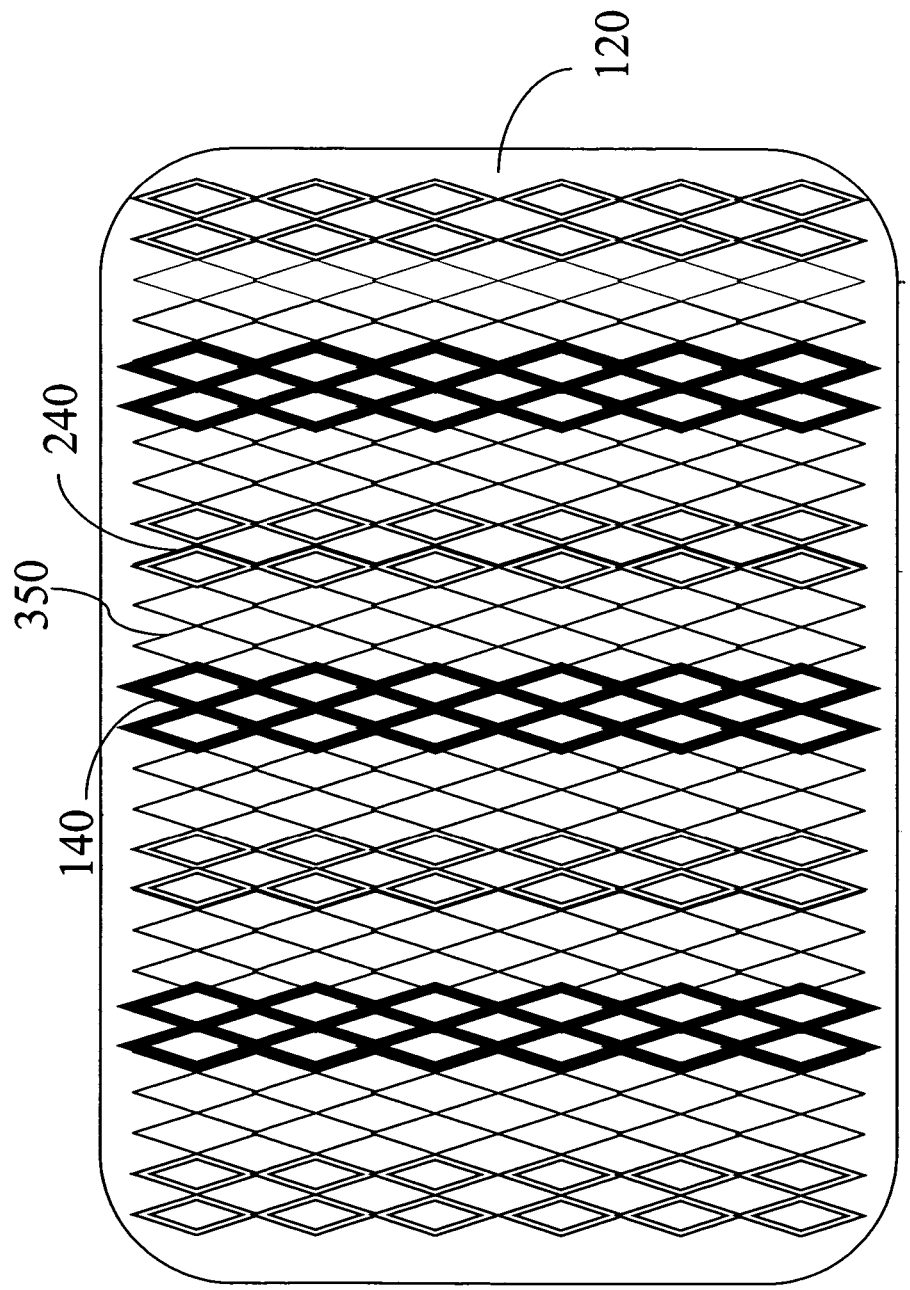
FIG. 10 is a top view of one embodiment in accordance with the invention showing the conductive electrodes 140 and 240 connected by electrically insulated connecting wire 350 embedded in the carrier layer 120.

FIG. 10 is a top view of one embodiment in accordance with the invention showing a device made of a zinc mesh having conductive electrodes 140 (shown in bold lines) and electrodes 240 (shown in double lines) connected by electrically insulated connecting wires 350 (shown in single lines) embedded in the carrier layer 120. The conductive electrodes 140 are uncoated regions of the zinc mesh. The conductive electrodes 240 is prepared by coating the designated portion of the zinc mesh with a silver-silver chloride ink. The electrically insulated connecting wire 350 is prepared by coating the designated portion of the zinc mesh with an electrically insulating paint, ink, or polymer solution.

Figure 11:
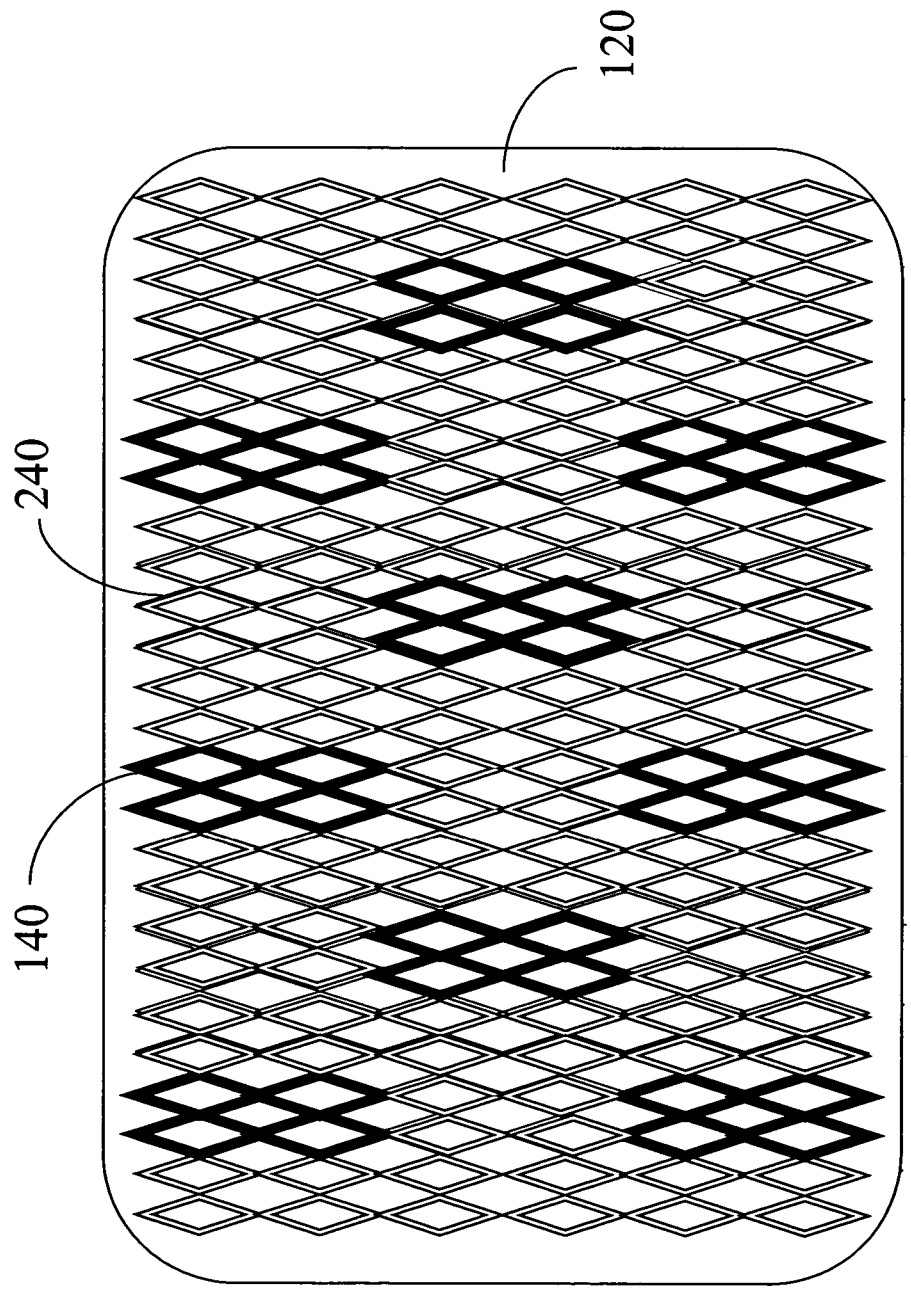
FIG. 11 is a top view of one embodiment in accordance with the invention showing the conductive electrodes 140 and 240 embedded in the carrier layer 120.

FIG. 11 is a top view of one embodiment in accordance with the invention showing the conductive electrodes 140 and 240 embedded in the carrier layer 120. The conductive electrodes 140 are made of a piece of zinc mesh. The conductive electrodes 240 are prepared by coating the designated portion of the zinc mesh with a silver-silver chloride or silver ink, or by other silver depositing methods such as electroless deposition (chemical reduction deposition), electroplating, plasma spray, or vacuum deposition. Elimination of the electrically insulated connecting wire 350 in this design would simplify the manufacturing process. The location, pattern, shape, and size of the electrode of metallic silver, silver-silver chloride or silver-silver oxide may vary depending on the need of a particular products.

Zinc mesh (or "expanded zinc" as common called in battery and anti-corrosion fields) may be prepared from a thin zinc foil with mechanical perforation and subsequent expansion into net-like patterns. The major advantages of a zinc mesh anode in the galvanic device of the present invention are its ability of forming and retaining the desirable mask/patch shape by a user, stretching by a user toward any directions to form mask/patch of desirable size; and being breathable.

It should be noted although the use of zinc mesh is described here as an example of electrode designs, other aforementioned materials suitable for galvanic couple formation and for conductive electrodes can also be made into a mesh or an expanded form to provide the same function.

Zinc mesh also has the ability to conform to the shape of the membrane surface (e.g., the shape of an individual's face) by gently pressuring it, and to retain this shape. This capability makes it uniquely suitable for a facial mask or certain skin patches to better fit the contours of certain anatomic features of the face (e.g., a nose patch) or body areas. This unique feature also assists in better electric contact and may also reduce dependence on using adhesives to affix the device to the skin.

It is also highly convenient and desirable to a consumer if a facial mask or patch can be stretched to different sizes in order to cover a particular skin area without compromising its electric performance. A zinc mesh anode (or other mesh conductive electrode) is uniquely capable to fulfill this consumer need. In another embodiment, the mesh is not expanded before use so that the device is smaller and more compact for easy storage and carrying. Rather, it is stretched open to a desired size during application by a consumer.

Good breathability is important for a facial mask or a patch of relatively large size, especially if the device is designed to be worn by a user for an extended period of time (e.g., longer than one half hour such as overnight). In order to make aforementioned device stretchable and/or breathable, the carrier layer 120 and backing layer 160 should also be stretchable and breathable, such as stretchable woven and nonwoven fabric materials.

In another embodiment, the backing layer 160 in FIGS. 3–5, can be perforated or eliminated entirely for a mask or patch device, which is especially suitable for the application of short duration, e.g., from about 5 to about 30 minutes. As water in the carrier composition evaporates, the electric conductance and the electric current decrease. Eventually, the electric current will significantly diminish, providing in essence a self-terminating device to serve as a safety measure for the user to prevent any unintentional over-exposure of the skin to the electric current and potential resulting skin damage.

One example of such a self-terminating device is a galvanic cloth facial mask made with a zinc mesh partially coated with silver-silver chloride ink, which is placed in between a backing film/housing (e.g., a perforated or nonperforated polyethylene film) and a nonwoven fabric (e.g., a polyester and/or rayon nonwoven sheet) using a binding process based on heating, ultrasound or other mechanism. Prior to application, a liquid or semisolid carrier composition containing ionic and non-ionc active agents and other optional electrolytes is applied to the nonwoven side of the device to activate the galvanic power source. The galvanic device is then pressed onto the user's face with the nonwoven side in direct contact with the skin. Alternatively, the active agents and other optional electrolyte may be incorporated in nonwoven layer during manufacturing process in an anhydrous state. In use, the device can be applied to water-wetted face, and the water will dissolve the active agents and electrolytes to activate the galvanic current. The anhydrous active agents may be in the form of dry powder immobilized onto the fibers of the nonwoven, or dissolved first in an organic solvent (e.g., polyethylene glycol, propylene glycol, glycerin, and/or alcohol) to form a non-conductive or very low conductive solution, which is absorbed in the nonwoven layer.

The zinc anode materials may be manufactured with a wide variety of manufacturing process, including, but not limited to, metal processing, electroless deposition, electroplating, plasma spray, vacuum deposition, print processes such as screen printing using a zinc conductive ink, textile or nonwoven technologies. Similarly, other conductive metal materials, such as silver-silver chloride, silver-silver oxide, copper, magnesium, aluminum alloys of zinc, magnesium, copper and aluminum, may be manufactured into the aforementioned electrode forms using the manufacturing processes disclosed above.

Topical Compositions Containing Galvanic Pairs

In one embodiment, the present invention features a topical composition containing a first conductive metal particulates (such as fine flakes, wires/fibers or metal-coated fibers) selected from zinc, aluminum, copper, and their alloys; and a second conductive metal particulates (such as fine flakes, wires/fibers or metal-coated fibers) selected from silver, copper, gold, and their alloys. The first and second metal particulates can be selected from aforementioned electrode materials to form galvanic couples. Upon contact, the first conductive metal and the second conductive metal form a galvanic pair, generates electric current, and electrochemically generates ions. In a further embodiment, the difference of the standard potentials of the first conductive metal and the second conductive metal is at least about 0.1 V, such as at least about 0.5 V. For example, upon contact with a first conductive metal that contains zinc (such as fine zinc wires, zinc flakes or polymer fibers coated with zinc) and a second conductive metal that contains silver (such as a fine silver wires/fibers, silver flakes, or polymer fibers coated with silver), the composition generates electric current and zinc ions within the topical composition.

The composition may additionally contain an active agent, such as an anti-acne agent (such as salicylic acid, benzoyl peroxide, retinoic acid and/or retinol). The topical composition containing the first metal and the second metal is preferably a semi-solid dosage form (such as a gel, a hydrogel, a water-in-oil emulsion, an oil-in-water emulsion, a cream, a lotion, an ointment, a multi-emulsion, a liposome, and/or a microcapsule formulation), and may contain the aforementioned fluid suspending or fluid absorbing materials. The topical composition may be prepared as such that one of the conductive metal is formulated in a separate phase from other conductive metal, for example, the first conductive metal (e.g., zinc flakes) is formulated in the discontinuous oil phase of an oil-in-water emulsion (e.g., a cream), while the second conductive metal (e.g., silver flakes) is formulated in the continuous aqueous phase of the emulsion. The topical composition of the present invention may also further contain a humectant (such as glycerin, propylene glycol, polyethylene glycol, sorbitol and/or urea) and aforementioned electrolytes to maintain certain moisture level and conductivity of the skin.

In one embodiment, during storage of such a topical composition, the first conductive metal and the second conduct metal are suspended substantially apart in a semi-solid composition (e.g., are not in contact with each other). Upon application to the membrane (such as the skin or mucosa) and partial drying of the liquid carrier, the contact of the first conductive metal and the second conductive metals results in galvanic couple formation and generation of electric current and metal ions of the first conductive metal, which provides benefits to the membrane such as antimicrobial, anti-inflammation, wound healing, iontophoretic delivery of active agents, tissue stimulation, and/or sebum reduction.

In one embodiment, the wires/fibers, flakes of conductive metals, or polymer fibers coated with the conductive metals are fine enough that they can be suspended in the semi-solid compositions during storage. In a further embodiment, they are in elongated shapes. The advantages of elongated shapes of the conductive metals (e.g., fine wires/fibers, flakes and polymer fibers coated with the conductive metals) include a lower apparent density and, therefore, a better floating/suspending capability in the topical composition; a higher probability of connected with each other when low concentrations of the conductive metals are used; and a wider and deeper range of the membrane tissue (e.g., the skin) that the galvanic current travels through and provides the benefits to.

In one embodiment, the first and second conductive metal particles are formulated into different compositions and are stored in separate compartments of a dual chamber dispensing package. For example, the less chemically stable (e.g., more oxidizable) zinc or its alloy particulates may be formulated in an anhydrous, essentially non-conductive composition with organic solvents such as polyethylene glycols, propylene glycol, glycerin, liquid silione and/or alcohol, or other pharmaceutically-acceptable organic solvents. The more chemically stable (e.g., less oxidizable) silver and silver chloride particulates may be formulated in an aqueous composition. The active agents may be formulated into either composition depending on their chemical stability and solubility. In use, the compositions are dispensed from dual chamber package (e.g., dual chamber pump, tube, pouch, bottle, etc.) and mixed prior or during application to the skin to form galvanic couples in situ to generate galvanic current and to treat the skin conditions.

In another embodiment, the aforementioned galvanic couples are manufactured as particulates to be incorporated into topical compositions. The particulates may be of any shape, including but not limited to, spherical or non-spherical particles or elongated or flattened shapes (e.g., metal or metal-coated spheres, hollow metal or metal-coated spheres, short metal-coated fibers or fabrics, and flakes), regular shapes (e.g., metal crystals), and irregular shapes (e.g., aggregated spheres). In one embodiment, the particulates have an average particle size of from about 1 micrometer to about 2 centimeters. What is meant by the particle size the maximum dimension in at least one direction. In one embodiment, the particulates have an average particle size of from about 1 micrometer to about 2 millimeters for non-elongated shapes. In another embodiment, the particulates with elongated shapes have an average particle size from about 10 micrometers to about 2 centimeters such as from about 100 micrometers to about 50 millimeters. For example, a polymer fiber of about 100 micrometers to about 10 millimeters in length may be coated partially with silver or silver-silver chloride on one end (or only on certain portions of the fiber), and zinc on the other end (or on the remaining portions). In another example, the polymer fiber is coated completely with the first conductive metal (e.g., silver-silver oxide or silver-silver chloride), and one end (or certain portions of the fiber) is coated with the second conductive metal (e.g., zinc or magnesium).

In practice, silver-coated polymer fibers manufactured by Noble Fiber Technologies, Inc. (Clarks Summit, Pa.) may be coated with zinc using methods such as conductive zinc ink printing, electroplating, electroless deposition, vacuum deposition, and spray coating. Alternatively, a metallic zinc or magnesium particulate (e.g., bead or thin wire) may be coated at one end (or at certain portions) with silver-silver oxide or silver-silver chloride. Spherical or non-spherical particles with an average particle size ranging from about one micrometer to about 5 millimeters may be partially covered with the first and second conductive metal coatings in a similar fashion.

The coating methods for such first and second conductive metals in preparing the galvanic couples may be electroless deposition, electric plating, vacuum vapor deposition, arc spray, conductive metal ink, and other known metal coating methods commonly used in electronic and medical device manufacturing processes. The galvanic couple particulates are preferably stored in aforementioned anhydrous forms, e.g., as a dry powder or immobilized in a fabric with binding agents, or as an essentially anhydrous non-conducting organic solvent composition (e.g., dissolved in polyethylene glycols, propylene glycol, glycerin, liquid silicone, and/or alcohol). The galvanic particulates have great versatility in applications, and can be used in many consumer and medical products such as patches, bandages, masks, garments, cloths, socks, bed sheets (e.g., by immobilized into the carrier or fabric), spread-on facial mask composition (such as a paste, cream or gel), creams, lotions, gels, shampoos, cleansers, powders, or incorporated into personal and medical products such as toothbrushes, dental flosses, wound dressings, diapers, sanitary napkins, dry wipes, pre-moistured wipes (with aforementioned anhydrous solvents), tampons, and rectal and vaginal suppositories. The galvanic particulates may also be incorporated into transdermal drug delivery patches to enhance drug penetration into the skin by iontophoresis and to reduce skin irritation by electric stimulation and electrically generated beneficial ions such as zinc ions.

EXAMPLE 1

Carriers

Examples of several carriers, including the weight percentage range of the ingredients of such carriers, are set forth in Table 1.

TABLE 1

| Component | Percent by Weight of the Carrier | | | | | |
| --- | --- | --- | --- | --- | --- | --- |
| | No. 1 | No. 2 | No. 3 | No. 4 | No. 5 | No. 6 |
| Salicylic acid | 0.1–10 | 2 | 2 | 0 | 0 | 0.1–10 |
| Benzyl peroxide | 0 | 0 | 0 | 0.5–10 | 0 | 0 |
| Sulfur | 0 | 0 | 0 | 0 | 3 | 3 |
| Resorcinol | 0 | 0 | 0 | 1 | 1 | 1 |
| Benzalkonium chloride | 0–2 | 0.1 | 0.1 | 0–2 | 0–2 | 0–2 |
| Benzethonium or methylbezethonium chloride | 0–2 | 0 | 0 | 0–2 | 0–2 | 0–2 |
| Cetylpyridium chloride | 0–2 | 0.1 | 0.1 | 0–2 | 0–2 | 0–2 |
| Phospholipid CDM | 0–40 | 5 | 5 | 0–40 | 0–40 | 0–40 |
| Hydrogen peroxide | 0–30 | 0 | 3 | 0–30 | 0–30 | 0–30 |
| Buffer (citrate, lactate, or phosphate salts | 0–10 | 2 | 2 | 0–10 | 0–10 | 0–10 |

TABLE 1-continued

| Component | Percent by Weight of the Carrier | | | | | |
|---|---|---|---|---|---|---|
| | No. 1 | No. 2 | No. 3 | No. 4 | No. 5 | No. 6 |
| of sodium, potassium, or lithium | | | | | | |
| Gelling agent (e.g., polyacrylates, cellulose, natural or synthetic gums, or polyacrylamide) | 0–20 | 5 | 5 | 0–20 | 0–20 | 0–20 |
| Chelating agent (e.g., EDTA) | 0–2 | 0.1 | 0.1 | 0–2 | 0–2 | 0–2 |
| Propylene glycol | 0–30 | 20 | 15 | 0–30 | 0–30 | 0–30 |
| Polyethylene glycol | 0–50 | 0 | 0 | 0–50 | 0–50 | 0–50 |
| Polypropylene glycol | 0–40 | 0 | 0 | 0–40 | 0–40 | 0–40 |
| Ethyl alcohol | 0–50 | 0 | 15 | 0–50 | 0–50 | 0–50 |
| Isopropyl alcohol | 0–50 | 0 | 0 | 0–50 | 0–50 | 0–50 |
| Dimethyl isosorbide | 0–20 | 2 | 0 | 0–20 | 0–20 | 0–20 |
| Isopropyl myristate | 0–30 | 1 | 1 | 0–30 | 0–30 | 0–30 |
| Purified water | Qs to 100 | Qs to 100 | Qs to 100 | Qs to 100 | Qs to 100 | Qs to 100 |

In order to evaluate the proposed mechanism of action for the electrochemically generated beneficial agents, an in vitro microbiologic study was conducted to investigate effect of electrolysis on *P. acne* inhibition in certain electrochemical systems; and an in vivo study was conducted in human volunteers using a commercial iontophoresis device.

EXAMPLE 2

In vitro Inhibition of *P. acnes* by Electrolysis

A BacT/ALERT system (BioMerieux, Inc., Durham, N.C.) was used in the *P. acnes* inhibition experiment. Briefly, 40 ml of an anaerobic casein and soy based broth culture medium in a bottle (BacT/ALERT SN, Organon Tekniks Corp., Durham, N.C.) was inoculated with *P. acnes*. The fully automated BacT/ALERT system was used to detect *P. acnes* growth over a 14-day study at 35° C. by continuous monitoring of $CO_2$ production using an optical calorimetric sensory system. A selected pair of the electrodes (Table 2, Columns 2 and 3) was disinfected with 70% isopropyl alcohol, and inserted through the rubber stopper into the culture medium in a nitrogen glove box. Some electrodes were connected to the poles of a battery (either 1.5 or 3V as indicated in Table 2, Column 3) for 30 minutes. The electrodes were then immediately removed from the BacT/ALERT bottle, which was then placed into the automated incubation and monitoring system for two weeks. Other elecrodes (i.e., Nos. 3 & 5 in Table 2), were not connected to an external battery, but rather were directly connected to each other at their ends outside the BacT/ALERT bottle to form galvanic couple. The electrodes of these galvanic couples (i.e., Nos. 3 & 5) remained in contact with the culture medium in the bottle during the 14-day study.

Zinc as the positive electrode (anode), with various materials as the negative electrode (cathode), was evaluated through the test conditions 1 to 7 (No. 1–7 in Column 1). Column 4 shows the voltage applied to the conductive electrode by the external battery. However, by simply connecting two conductive electrode materials, a voltage was also generated just from the galvanic pair. For example, zinc-silver/silver chloride galvanic couple has a voltage of 0.9849V or about 1V ($Zn^{2+}+2e^-=Zn$, standard potential: $-0.7626V$, and $AgCl+e^-=Ag+Cl^-$, standard potential: 0.2223V) and zinc-copper galvanic couple has a voltage of about 1.1–1.3V ($Cu^{2+}+2e^-=Cu$, standard potential: 0.340V, and $Cu++e^-=Cu$, standard potential: 0.520V) Reference: Electrochemistry Handbook, 1995, Table 14.1, McGraw-Hill, Inc. New York, N.Y.).

In the test condition No. 7, the electrodes (i.e., zinc-silver/silver chloride galvanic couple) were taken from a commercial iontophoresis device (IontoPatch, SP, Birch Point Medical, Inc., Oakdale, Minn.). The IontoPatch is an iontophoresis device powered by a galvanic couple "battery strip" made of zinc and silver/silver chloride in a bandage-like device. In this experiment, the "battery strip" in the IontoPatch was taken out of the bandage-like device, and placed into the BacT/ALERT bottle. The electrodes of the commercial zinc-silver/silver chloride galvanic couple (No. 7) remained in the BacT/ALERT bottle through out the entire two-week experiments. Test conditions of Nos. 15–17 were positive controls (i.e., without electrodes): Test condition No. 15 used a concentrated *P. acne* culture that was used to inoculate the rest of the culture medium in each BacT/ALERT bottle to *P. acnes* counts of $10^6$ per ml and Test conditions No. 16 and No. 17 used the inoculated culture medium of *P. acnes* counts of $10^6$ per ml (with the rubber stoppers of No. 16 additionally being punctured in a way similar to the rest of electrode-tested conditions in order to eliminate any false *P. acnes* inhibition results due to potential environmental oxygen entry into the test bottle and affecting anaerobic *P. acnes* growth).

TABLE 2

| No. | Positive Electrode | Negative Electrode | Voltage applied by connected to a battery or batteries | Average time to Positive P. acnes Growth (days) | Number positive/ number tested |
|---|---|---|---|---|---|
| 1 | Zinc | Silver/Silver Chloride | 3 V | — | 0/3 |
| 2 | Zinc | Zinc | 3 V | — | 0/1 |
| 3 | Zinc | Copper | None[a] | — | 0/2 |
| 4 | Zinc | Copper | 1.5 V | — | 0/1 |
| 5 | Zinc | Silver/Silver Chloride | None[a] | — | 0/2 |
| 6 | Zinc | Silver/Silver Chloride | 1.5 V | — | 0/2 |
| 7 | Zinc | Silver/Silver Chloride | None[a] | —[b] | 2/6 |
| 8 | Copper | Silver/Silver Chloride | 3 V | — | 0/3 |
| 9 | Copper | Copper | 3 V | — | 0/2 |
| 10 | Platinum | Silver/Silver Chloride | 3 V | 1.6 | 2/2 |
| 11 | Platinum | Platinum | 3 V | 1.1 | 1/1 |
| 12 | Silver | Silver/Silver Chloride | 3 V | 5.7[c] | 2/3 |
| 13 | Silver | Silver | 3 V | 2.8d | 2/2 |
| 14 | Silver/Silver Chloride | Silver/Silver Chloride | 3 V | 3.0 | 2/2 |
| 15 | None | None | None | 0.8 | 2/2 |
| 16 | None | None | None | 1.4 | 2/2 |
| 17 | None | None | None | 1.3 | 2/2 |

[a] The conductive metal electrodes were not connected to any battery, but to each other. Therefore, there is a voltage across the two electrode dictated by the galvanic pair.
[b] A total of 6 samples were tested; 4 negative and 2 positive (0.6d & 0.8d); the positive ones were very likely due to bacterial contamination since they were detected faster then the positive control samples (Nos. 16 & 17), and therefore were omitted.
[c] Out of 3 samples, two positive (4.1d & 7.3d) were averaged The zinc anode was surprisingly found to almost completely inhibit P. acne growth during the 14-day incubation study at the all of the voltage conditions tested (Nos. 1–7; in No. 7, two of the six commercial galvanic couples showed positive P. acnes growth probably due bacterial contamination, see Note C of Table 2). The copper anode was also found to significantly inhibit P acnes growth (Nos. 8–9). Under these experimental conditions, the platinum anode showed little P. acne inhibition effect and the silver or silver/silver chloride anodes provided only a weak P. acne inhibition. Since all the positive control conditions (Nos. 15–17) showed positive P. acnes growth less than two days after the beginning of the study, the negative P. acnes growth can be attributed to the inhibition effect of the electrochemically generated species or electric current passage through the culture medium. Because electric current passage in Nos. 10–14 failed to show strong P. acnes inhibition as those in Nos. 1–9, the observed bacterial inhibition in Nos. 1–9 were likely due to certain electrochemical reactions occurred at the anode, namely, when zinc and copper were used as the anode. It was also unexpected that the silver ions released from silver or silver/silver chloride anode under these experimental conditions failed to show the same P. acnes inhibition (Nos. 12–14), since silver ion is well-known anti-microbial agent. See. e.g., Spacciapoli et al. ("Antimicrobial activity of silver nitrate against periodontal pathogens.", J Periodontal Res 36: 2, 108–13, April, 2001). It was surprising that, in the absence of external battery (Nos. 3, 5 and 7), a pair of electrodes of galvanic couple with zinc as anode were sufficient to inhibit P. acnes growth during the entire two week study.

EXAMPLE 3

In vitro Electrode-salicylic Acid Compatibility

The following experiment was conducted to determine the compatibility of electrodes with salicylic acid. A pair of test electrodes was immersed in 5 ml of 1.5% salicylic acid solution (solvent 50% ethanol/50% water). A pre-determined voltage was applied to the electrodes (by connecting the electrodes to a battery or batteries) for certain length of time as indicated in Table 3. Observations were made on color change of the test solution.

The solution with the zinc anode showed no discoloration, indicating good compatibility with salicylic acid during the passage of electric current. Use of the platinum anode unexpectedly resulted in discoloration, indicating incompatibility with salicylic acid under this experimental condition.

TABLE 3

| Electrode Material | | Test | | Observation |
|---|---|---|---|---|
| Anode (+) | Cathode (−) | Voltage (V) | Duration (min) | Solution color change |
| Platinum | Platinum | 3 | 10 | Colorless → yellow |
| Platinum | Platinum | 9 | 10 | Colorless → brown |
| Zinc | Platinum | 1.5 | 10 | No color change |
| Zinc | Platinum | 3 | 10 | No color change |
| Zinc | Platinum | 9 | 30 | No color change |

EXAMPLE 4

In vivo Human Iontophoresis Study

An in vivo study was conducted in human volunteers using a commercial iontophoresis device (IontoPatch®, Model: SP, Birch Point Medical Inc., North Oakdale, The study recruited the healthy female volunteers with oily skin, aged from 20–45 years. The sebumeter reading from each subject's forehead was at least greater than 150 $mg/cm^2/hr$. The study was blind and controlled. Briefly, an IontoPatch® with a voltage of 1 volt, an operating current of 0.06 mA, and an active treatment area of 1.25 $in^2$, was applied to the treatment site of the human subject (e.g. forehead). The positive electrode and negative consisted of zinc and silver/silver chloride (Ag/AgCl) material, respectively. Both electrodes were filled with saline (0.9% NaCl). As soon as the saline solution was added into the different electrodes, the electric patch begin to function. The patch was left on the treatment area overnight (e.g., approximately 8 hours).

The following evaluations were conducted: (i) the effects of electrolysis on the skin condition were monitored using a normal photography and (ii) The change in p. acnes counts was determined through analyzing the cup wash solution for the treatment site before and after wearing the patch overnight. The cup wash micro sampling procedure was performed as follows: a cylindrical cup (2.1 cm diameter and 2.5 cm height) having two open ends was fastened onto the treatment area. The treatment area inside the cylinder was then washed with 2 ml of cleansing buffer (sterile 0.075M Phosphate Buffer containing 0.1% Triton X-100) while the same area with a sterile polished glass. The wash solution was then collected. This washing procedure was then repeated. The two collected samples were pooled and used in the P-acnes analysis.

The P. acnes counts were determined by Spiral Plating the scrub samples anaerobically in Actinomyces Agar for 5 days, and the predominant contaminants on the spiral plates were Gram stained and identified using the VITEK System. Using an automated colony counter, the P-acne count per mL of each sample buffer was determined.

After only one overnight patch application, P. acne quantification measurement on the treatment area shows a 45% P. acne reduction relative to the baseline under the zinc anode and 30% under the Ag/AgCl cathode. After four consecutive overnight patch applications, photo images displayed the clear evidences of significant reduction in the color and size of post-acne hyperpigmentation spot under the zinc electrode. This test subject had a post-acne hyperpigmentation spot at the test skin site. The appearance of the hyperpigmented spot was improved from a very dark color to a lighter color.

Also, after four consecutive overnight patch applications, photo images also displayed the evidence of significant reduction in the color and size of an acne pimple under the Ag/AgCl electrode. This test subject had an acne pimple at the test skin site. The redness of the pimple was rapidly reduced from very red color to become almost invisible while the pimples at the non-treated skin area remained largely unchanged.

EXAMPLE 5

In vivo Human Iontophoresis Study Using Histamine Hydrochloride as Marker

An in vivo study was conducted in three human volunteers using a galvanic zinc-silver/silver oxide device to deliver histamine hydrochloride as a marker into the skin. Histamine-induced skin erythema and itchiness were recorded during and after the study. The study recruited two healthy male and one female volunteers with ages ranging 41 to 49 years. The galvanic devices were prepared by cutting a thin zinc foil (0.25 mm thick, Alfa Aesar, Word Hill, Mass.) into rectangular piece (2.5 cm wide & 3 cm long). A silver ink (Silver Print, M.G. Chemicals, Toronto, Ontario, Canada) was painted onto one side of the zinc foil as a 0.5 cm wide stripe along the long-axis at the center. The ink was air-dried to produce the silver electrode stripe on the zinc foil. Two rectangular adhesive Scotch® tape stripes of 0.5 cm wide and 3 cm long were placed on the both sides of the silver electrode stripe creating an electric insulating gap on the surface (electrode gap=0.5 cm). A rectangular piece of nonwoven fabric (50% Rayon/ 50% PET, 75 gsm, PGI Polymer Group Inc., Landisville, N.J.) of 3 cm wide and 3.5 cm long was placed over the zinc-silver electrode side of the zinc foil. A rectangular adhesive backing film of 4 cm wide and 5 cm long was affixed to the opposite side of the zinc foil to complete the zinc-silver galvanic device.

A second type of the zinc-silver galvanic device without and electric insulating gap on the surface (electrode gap=0 cm) was prepared by simply omitting the addition of the adhesive Scotch® tape. A third type (control) patch was prepared by using only the zinc foil, the nonwoven pad, and the adhesive backing film to construct the device.

To begin histamine iontophoresis, 0.8 ml aqueous solution of 0.1% histamine hydrochloride (Sigma-Aldrich, St. Louis, Mo.) was added to each device, which was then affixed to the forearm skin of each volunteer for 30 minutes.

At the end of the study, red spots (histamine induced erythema) appeared under both zinc-silver galvanic patch devices, which disappeared within about one half hour. A close examination showed the red spots around the hair follicles. There was also itchiness reported at the galvanic patch sites reported during the patch application. In contrast, there were no change in skin color under, nor any itchiness reported with, the control patch devices.

EXAMPLE 6

In vivo Human Iontophoresis Study Using Histamine Hydrochloride with a Galvanic Nose Patch Comprising Zinc Mesh As a continuation of the human in vivo study in the previous example, a galvanic patch device (designated here as "Test Device D") comprising a zinc mesh (diamond openings of 1 cm long & 0.4 cm wide, Dexmet Corporation, Naugatuck, Conn.) instead of zinc foil was prepared with the same dimension and procedure as the galvanic device (gap electrode=0) in EXAMPLE 5. The device thus prepared resembled to the design shown in FIG. 11 with three parallel electrodes: the silver electrode in the center and zinc electrodes on both sides. Two male volunteers participated this study using a similar test conditions as in EXAMPE 5. One Test Device containing 0.8 ml of 0.1% histamine hydrochloride was applied to the nose of each volunteer for 30 minutes. Itchiness was reported within 5 minutes of the nose patch application, indicating rapid delivery of histamine into the relatively larger skin pores on the nose. For both test subjects, pronounced erythema was observed at the skin site under the nose patch after patch removal at the end of the study, in comparison to the study conducted on the forearm skin.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

The invention claimed is:

1. A method of treating pores on the skin, said method comprises topically applying a composition to said skin, said composition comprising a first conductive electrode in the form of a particulate and a second conductive electrode partially coated on said particulate wherein the difference of the standard potentials of said first conductive electrode and said second conductive electrode is at least 0.2 V, wherein said first conductive electrode and said second conductive electrode are in electric communication, wherein both said first conductive electrode and said second conductive electrode are in ionic communication with said skin, and wherein said method of treating pores on the skin is selected from the group consisting of cleansing pores on the skin, reducing sebum on the skin, reducing the appearance of blackheads on the skin, and reducing the appearance of pores on the skin.

2. A method of claim 1, wherein said first conductive electrode comprises zinc and said second conductive electrode comprises silver.

3. A method of claim 1, wherein said composition further comprises salicylic acid or a salt thereof.

4. A method of treating pores on the skin, said method comprising affixing to skin in need of such treatment a device comprising:
a housing having a skin contacting surface;
a first conductive electrode that is an anode;
a second conductive electrode that is a cathode; and
a carrier comprising an active agent;
wherein said first conductive electrode is in electric communication with said second conductive electrode, wherein first conductive electrode and said second conductive electrode are in ionic communication with said carrier, wherein said carrier is in communication with said skin through said skin contacting surface, wherein the difference of the standard potentials of said first conductive electrode and said second conductive electrode is at least 0.2 V, wherein the electrons that pass between said first conductive electrode and said second conductive electrode are generated as a result of said difference of the standard potentials, and wherein upon affixing said device to said skin, said device delivers said electric current from said first conductive electrode, through said carrier, through said skin, and through said carrier to said second conductive electrode, and wherein said method of treating pores on the skin is selected from the group consisting of cleansing pores on the skin, reducing sebum on the skin, reducing the appearance of blackheads on the skin, and reducing the appearance of pores on the skin.

5. A method of claim 4, wherein said housing contains both said first conductive electrode and said second conductive electrode.

6. A method of claim 5, wherein said active agent is salicylic acid or a salt thereof.

7. A method of claim 5, wherein said housing is a nonwoven substrate.

8. A method of claim 4, wherein said active agent is salicylic acid or a salt thereof.

9. A method of claim 4, wherein carrier is added to said device by the user prior to application to said skin.

* * * * *